United States Patent
Falb et al.

(12)

(10) Patent No.: US 6,512,092 B2
(45) Date of Patent: Jan. 28, 2003

(54) PROCESSES FOR COUPLING AMINO ACIDS USING BIS-(TRICHLOROMETHYL) CARBONATE

(75) Inventors: Eliezer Falb, Givaraim (IL); Tamar Yechezkel, Ramat-Gan (IL); Yoseph Salitra, Rehovot (IL)

(73) Assignee: Peptor Ltd., Rehovot (IL)

( * ) Notice: Subject to any disclaimer, the term of this patent is extended or adjusted under 35 U.S.C. 154(b) by 76 days.

(21) Appl. No.: 09/756,223

(22) Filed: Jan. 9, 2001

(65) Prior Publication Data

US 2001/0007037 A1 Jul. 5, 2001

Related U.S. Application Data

(63) Continuation of application No. PCT/IL99/00378, filed on Jul. 11, 1999.

(30) Foreign Application Priority Data

Jul. 12, 1998 (IL) .................................................. 125314

(51) Int. Cl.[7] .............................. C07C 1/10; C07C 1/04
(52) U.S. Cl. ....................................... 530/333; 530/334
(58) Field of Search ................................. 530/333, 334

(56) References Cited

U.S. PATENT DOCUMENTS 5,198,548 A  *  3/1993  Beylin et al. ................ 546/136

OTHER PUBLICATIONS

Database Caplus, DN 123:199391. Riviero et al. Synth. Commun. (1995), 25(14), 2185–8.*
Andre et al. Journal of Peptide Science (1997), 3(6), 429–441.*
Database Caplus, DN 122:188103. Suarez–Gea et al. J. Org. Chem. (1994), 59(13), 3600–3.*

* cited by examiner

*Primary Examiner*—Michael Borin
(74) *Attorney, Agent, or Firm*—Winston & Strawn

(57) ABSTRACT

A process is disclosed for using triphosgene as an efficient and effective coupling reagent during peptide synthesis, by in situ generation of amino acid chloride from a protected amino acid. This process is particularly useful for the coupling to sterically hindered amino acid residues, or for other difficult couplings. Furthermore, the same reagent can be used for the derivatization of peptides by formation of an amide bond between a free amine on a peptide and a carboxylic acid, or for the coupling of an amino acid to a solid support.

14 Claims, 10 Drawing Sheets

US 6,512,092 B2

PROCESSES FOR COUPLING AMINO ACIDS USING BIS-(TRICHLOROMETHYL) CARBONATE

CROSS-REFERENCE TO RELATED APPLICATIONS

This application is a continuation of the U.S. national stage designation of International Application no. PCT/IL99/00378 filed Jul. 11, 1999, the content of which is expressly incorporated herein by reference thereto.

FIELD OF THE INVENTION

The invention relates to a process for the in situ generation of amino acid chlorides utilizing bis-(trichloromethyl) carbonate, commonly known as triphosgene, and to methods of using this process for solid phase peptide synthesis and for derivatization of a solid support.

BACKGROUND OF THE INVENTION

In the field of peptide synthesis certain couplings are known as difficult couplings, especially those involving coupling to bulky or sterically hindered amino acid residues, such as N alkylated, C-alkylated and $C^\alpha$ branched amino acids. In order to obtain acceptable yields when these couplings are performed a variety of special coupling reagents have been developed. Among other known procedures, is the use of pre-formed amino acid chlorides to improve the outcome of the coupling reactions.

The general use of protected amino acid chlorides in solid phase peptide synthesis (SPPS) is limited mainly because of the fact that chlorides of fluorenylmethoxycarbonyl (Fmoc) amino acid having side chains protected with acid labile protecting groups, including but not limited to t-butyl (t-Bu), t-butoxycarbonyl (Boc) or trityl (Trt), have limited shelf stability. For example, chlorides of Fmoc-amino acids (AAs) with t-Bu-protected side chains could not generally be accommodated. In some cases (aspartic acid and glutamic acid) the chlorides could not be obtained and in other cases (tyrosine, serine, threonine) their shelf stability appeared insufficient for practical utilization. In addition, the preparation of chlorides derived from Fmoc- Lysine(Boc), Fmoc-Tryptophan (Boc), Fmoc-Cysteine(Trt), Fmoc-Glutamine (Trt) and Fmoc-Arginine 2,2,5,7,8-Pentamethyl chroman-6-sulphonyl (Pmc) is problematic because of side reactions and require special reaction conditions and purification (Carpino et al. *Acc. Chem. Res.* 29:268, 1996). This problem also hampers the general use of pre-formed Fmoc amino acid chlorides in automatic peptide synthesis. Despite these limitations, acid chlorides were used in SPPS especially for the assembly of hindered secondary amino acids (see Carpino et al. 1996 ibid and refs. within).

Coupling of protected amino acids to $N^\alpha$-alkylated amino acids was previously considered to be a difficult coupling both in solution and solid phase. This coupling was used in model peptides to demonstrate the efficiency of new, more effective, coupling methods. In these models, N-Methylated amino acids were used as nucleophiles, since coupling to N-Methylated amino acids having steric hindrance on the $C^\alpha$(e.g., N-methyl .valine and N-methyl Aminoisobutyric acid) was found to be much slower than to proline. Certain coupling agents and activation methods such as bromo-tris-pyrrolidino-phosphonium hexafluorophosphate (PyBroP) (Coste et al. *Tetrahetron Lett.* 31 669, 1990), 1-hydroxy-7-azabenzotriazole (HOAt)/O-(7-azabenzotriazol-1-yl)-1,1,3,3-tetramethyluronium hexafluorophosphate (HATU) (Carpino et al. *J Chem. Soc., Chem. Commun.* 201, 1994), urethane- protected N-carboxyanhydrides (UNCA) (Spencer et al. *Int. J. Pep. Prot. Res.* 40:282, 1992) and acid halides (Carpino et al., 1996 ibid) were specially recommended to achieve coupling to N-alkyl amino acids.

The acid chloride method was found to be a superior way to couple protected amino acids to sterically hindered amino acid derivatives, such as the N-alkyl amino acids during SPPS of backbone cyclic peptides. To overcome the limitations of the pre-formed acid chloride method and to allow its general use in SPPS, it would be advantageous to have an efficient and generally applicable method allowing the in-situ generation of Fmoc-AAs chlorides.

The reagent bis-(trichloromethyl)carbonate (BTC) (Councler, C. *Ber. Dtsch. Chem. Ges.* 13:1697, 1880) also named hexachlorodimethyl carbonate or "triphosgene" is a solid stable phosgene substitute equivalent to three moles of phosgene. Triphosgene has been used as an efficient carbonylating agent for liquid and solid phase synthesis of various aza-analogues of peptides containing aza-alanine, aza-aspartic acid and aza-asparagine residues (Andre et al. *J. Pep. Sci.* 3:429, 1997).

The use of triphosgene as a reagent for formation of isocyanates or other reactive species useful in peptide chemistry has also been disclosed (Eckert DE3440141, Nippon Kayaku JP10007623). The usefulness of triphosgene in preparation of various intermediates for pharmaceuticals has also been disclosed (Hoffmann et al. DD292452).

It is neither taught nor suggested in the art that the triphosgene reagent is suitable for the in-situ generation of protected amino acid chlorides, namely as a coupling agent in SPPS (for review see Cotarca et al. *Synthesis* 553, 1996)

Phosgene gas has long been a valuable asset to both lab and plant scale operations however the dangers of using it are also well documented, especially the respiratory hazards. Liquid trichloromethyl chloroformate, commonly known as "diphosgene" (Fridgen, L. N. and Prol, J. J., *J. Org. Chem.* 54:3231, 1989) which has already been used as a phosgene substitute, has proven useful in all common phosgene reactions, but being a liquid its transport and storage still impose considerable hazard. Being a crystalline solid (mp 81–83° C.), BTC is safer and easy to handle and therefore became the reagent of choice for all applications where phosgene chemistry is required (Cotarca et al. ibid). Synthetically, one mole of BTC yields three mole-equivalents of phosgene which reacts with hydroxyl, amine or carboxylic acid nucleophiles forming chloroformate, isocyanate or acyl chloride, respectively.

Considering all these features together with the fact that BTC is inexpensive and less susceptible to hydrolysis than phosgene, it is surprising that the use of BTC as a general coupling agent has not been considered.

Backbone cyclized peptide analogs

Backbone cyclization is a concept that allows the conversion of peptides into conformationally constrained peptidomimetics with desired pharmacological properties such as metabolic stability, selectivity and improved bioavailability (Gilon et al. *Biopolymers* 31:745, 1991; Byk et al. *J. Med. Chem.* 39:3174, 1996; Gilon et al. *J. Med. Chem.* 41:919, 1998). In backbone cyclization the $N^\alpha$ and/or $C^\alpha$ atoms in the peptide backbone are linked through various spacers. To synthesize N-backbone cyclic peptides a large number of orthogonally protected-finctionalized $N^\alpha$ alkyl amino acids (N- building units) were prepared (Bitan et al. *J. Chem. Soc., Perkin trans. I* 1501, 1997a; Muller et al. *J. Org. Chem.* 62:411, 1997). These units were incorporated into peptides by SPPS or solution methodologies and after orthogonal removal of the protecting groups from the ω-functions on the $N^\alpha$-alkyl they are cyclized. A critical step in the synthesis of N-backbone cyclic peptides is the coupling of protected amino acids to the sterically hindered secondary amine of the $N^\alpha$ (ω-functionalized alkyl) amino acid residue on the peptidyl-resin.

The synthesis of N-backbone cyclic peptides that incorporate $N^\alpha$ (ω-functionalized alkyl) Glycine building units were reported previously. In these cases couplings of the protected amino acids to the secondary amine of the Gly building unit attached to peptidyl resin were achieved by multiple couplings with benzotriazole-1-yl-oxy-tris-(dimethylamino)-phosphonium hexaflourophosphate BOP or PyBroP as coupling agents (Bitan et al.. *J. Pept. Res.* 49:421, 1997b; Byk et al., 1996 ibid).

Generally, the coupling of protected AAs to building units other than Gly (non-Gly backbone cyclic building units) were found to be difficult and even impossible.

It has been shown that the coupling of many Fmoc AAs to sterically hindered secondary amines including a variety of non-Gly building units attached to peptidyl-resin could be achieved in moderate to high yields using the acid-chloride method but not acid fluorides (Carpino et al. 1996 ibid) or other coupling agents such as PyBrOP (Coste et al., ibid), HOAt/HATU Carpino 1994 ibid), 2-(2-Oxo-1(2H)-pyridyl)-1,1,3,3-bispenta-methyleneuronium tetrafluoroborate (TOPPipU) (Henkleinet al. In ""Peptides 1990" Proc. of the 21th European Peptide Symposium", E. Giralt and D. Andreu, eds, pp. 67. ESCOM Leiden, 1990), UNCA (Spencer et al., 1992) and Mukaiyama reagent (Mukaiyama, T. *Angew. Chem., Int. Ed. Ingl.* 18:7078, 1979).

SUMMARY OF THE INVENTION

The present invention relates to a process for the improvement of difficult couplings in SPPS. The invention also provides a method for improving the yield of the desired stereoisomer in solid phase peptide synthesis. In addition, the invention further provides methods for facilitating multiple parallel synthesis (MPS).

The present methods are useful for attaching protected amino acids to functionalized solid supports or to attach biomedically important ligands to a peptide or peptidyl resin during SPPS. Furthermore, these methods can be used to cyclize peptides attached to a solid support, or to form a urea bond in the sequence or in the bridge of cyclized peptides.

According to the present invention, a process is provided for the in situ generation of protected amino acid chlorides, by use of an agent such as phosgene, diphosgene or more preferably triphosgene. The protected amino acid chlorides thus generated are particularly useful in the coupling of an amino acid residue to a peptide chain. They can also be used for the coupling of a carbohydrate moiety to a peptide chain.

The in situ generation of acid chlorides using the methods of the present invention thus further provides a process whereby other biologically important acids, including but not limited to glucoronic acid, DTPA, and DOTA, may be connected to a peptide chain through the amine backbone or through an amino acid side chain functionality.

It has now been found that in accordance with the principles of the present invention bis-(trichloromethyl) carbonate, also known by the trivial chemical name triphosgene, can be used for the in situ generation of protected amino acid chlorides. This process overcomes many of the problems encountered in difficult coupling steps in SPPS, particularly where the coupling step involves sterically hindered amino acid residues or bulky amino acid analogs.

Methods are provided for the use of BTC as a convenient and efficient coupling agent for difficult couplings in SPPS. These methods provide greatly enhanced yields of the desired product in SPPS with retention of configuration and without undesired side reactions and also facilitate the performance of multiple parallel peptide synthesis. These methods also facilitate the synthesis of complex peptide analogs with multiple cyclizations, e.g., bi- and tri- cyclic peptides.

One method according to the present invention provides a process of coupling an amino acid residue to a peptide chain comprising:

(i) providing an amino acid residue having a free carboxylic group and blocked amino group, optionally having additional blocked functional side chains;

(ii) reacting the blocked amino acid with bis-(trichloromethyl)carbonate in an solvent inert to this reaction to obtain an amino acid chloride;

(iii) neutralizing the free acid by addition of an organic base;

(iv) adding the resulting suspension containing the amino acid chloride to a compound selected from the group consisting of a peptide having a blocked carboxyl terminus and a free amino terminus, and a peptidyl resin having at least one free amino terminus;

(v) providing reaction conditions enabling the coupling of the amino acid chloride to the peptide to yield a peptide elongated by one amino acid residue.

A second method according to the present invention provides a process of coupling an amino acid residue to a solid support comprising:

(i) providing an amino acid residue having a free carboxylic group and blocked amino group, optionally having additional blocked functional side chains;

(ii) reacting the blocked amino acid with bis-(trichloromethyl)carbonate in a solvent inert to the reaction to obtain an amino acid chloride;

(iii) neutralizing the free acid by addition of an organic base;

(iv) adding the resulting suspension containing the amino acid chloride to a compound selected from the group consisting of a resin having at least one free amino terminus and a solid support having a functional group capable of binding the chloride;

(v) providing reaction conditions enabling the coupling of the amino acid chloride to the solid support.

A currently most preferred embodiment according to the present invention is summarized below in Scheme 1:

Scheme 1
Difficult coupling using BTC in solvent inert to this reaction

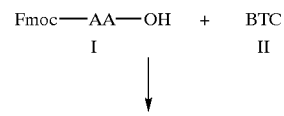

-continued

[Fmoc—AA—Cl]

III

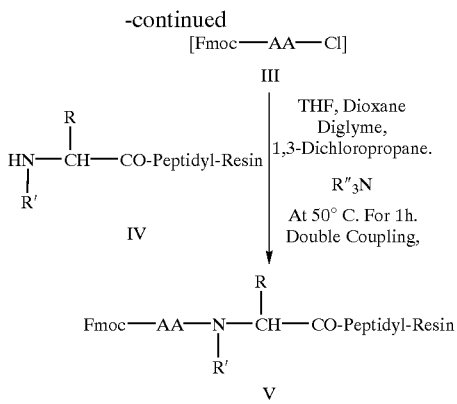

IV

R"₃N

THF, Dioxane
Diglyme,
1,3-Dichloropropane.

At 50° C. For 1h.
Double Coupling,

Fmoc—AA—N—CH—CO-Peptidyl-Resin
           |    |
           R'   R

V

BTC=Bis-(trichloromethyl)carbonate (triphosgene)
Fmoc-AA=Fluorenylmethoxycabonyl-proteinogenic-α-Amino Acid
R=Side chains of all proteinogenic α-amino acids
R'=CH3, $(CH2)_{n=2-4}$-NH-Alloc, $(CH2)_{n=2-3}$-COOAllyl
$R_3$"N=tertiary or aromatic amine

DETAILED DESCRIPTION OF THE INVENTION

Figure 1:
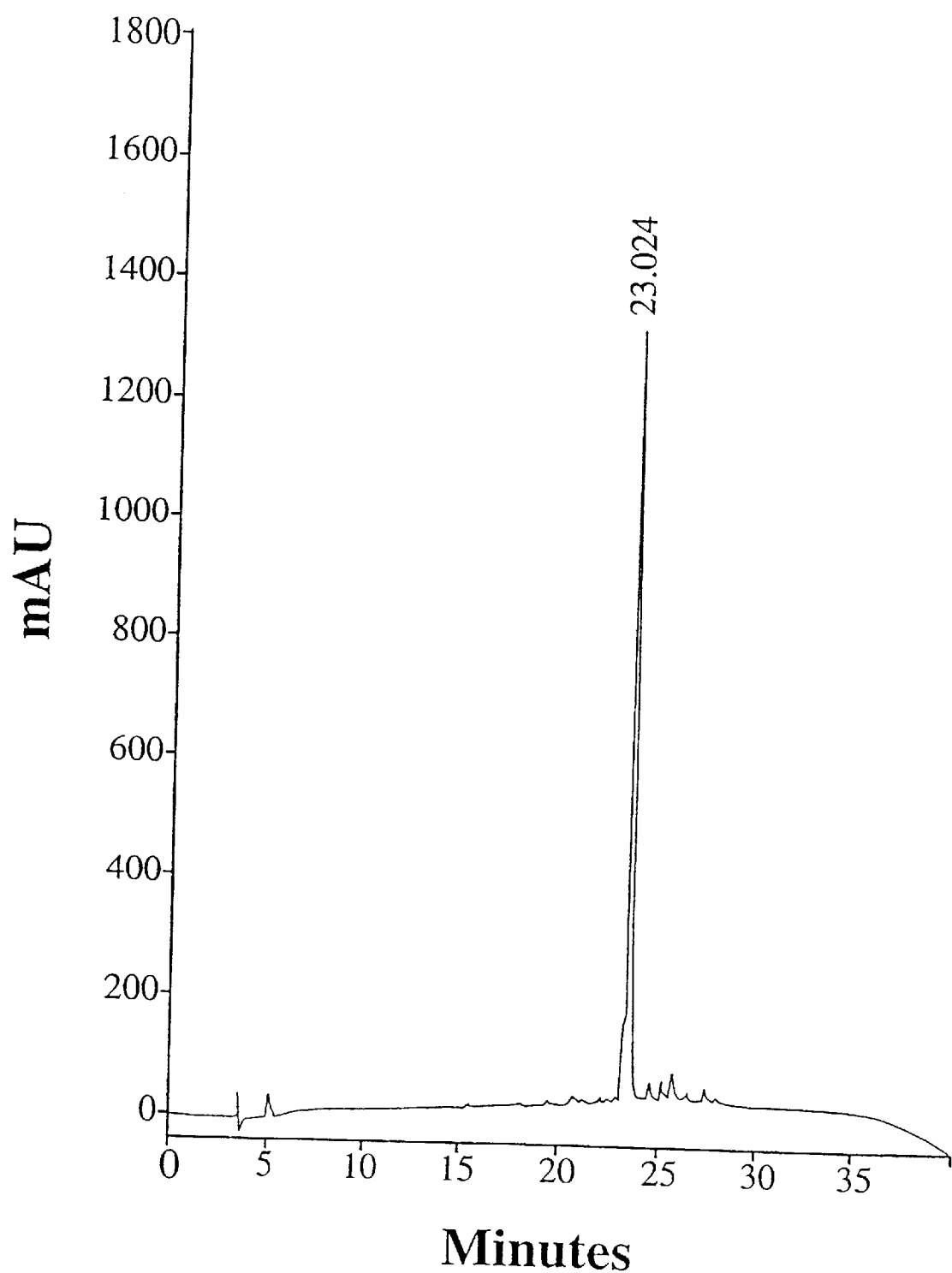
FIG. 1. HPLC chromatogram of the product obtained in example 38.
Figure 2:
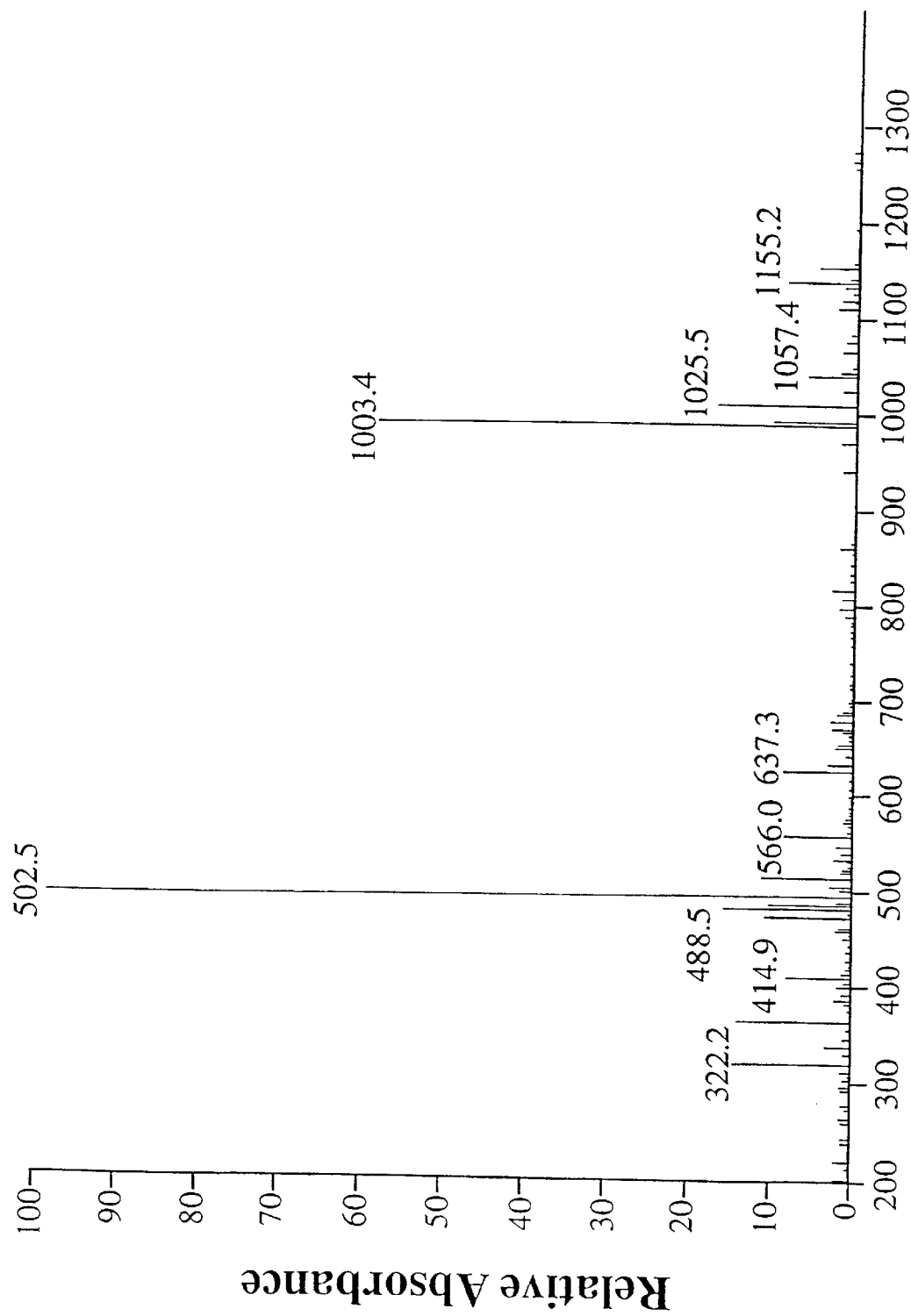
FIG. 2. Mass spectra analysis of the product obtained in example 38.
Figure 3:
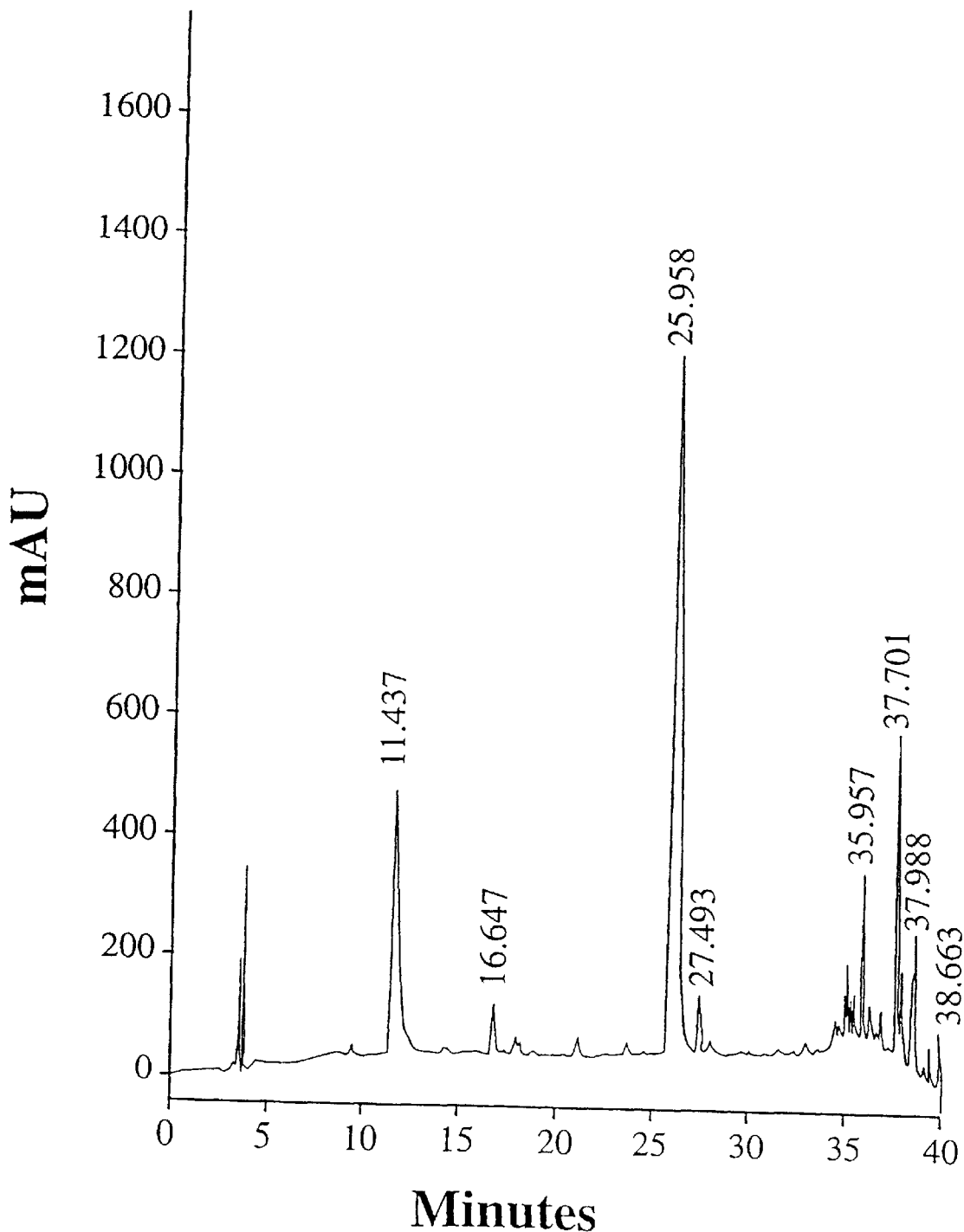
FIG. 3. HPLC chromatogram of the product obtained in example 49.
Figure 4:
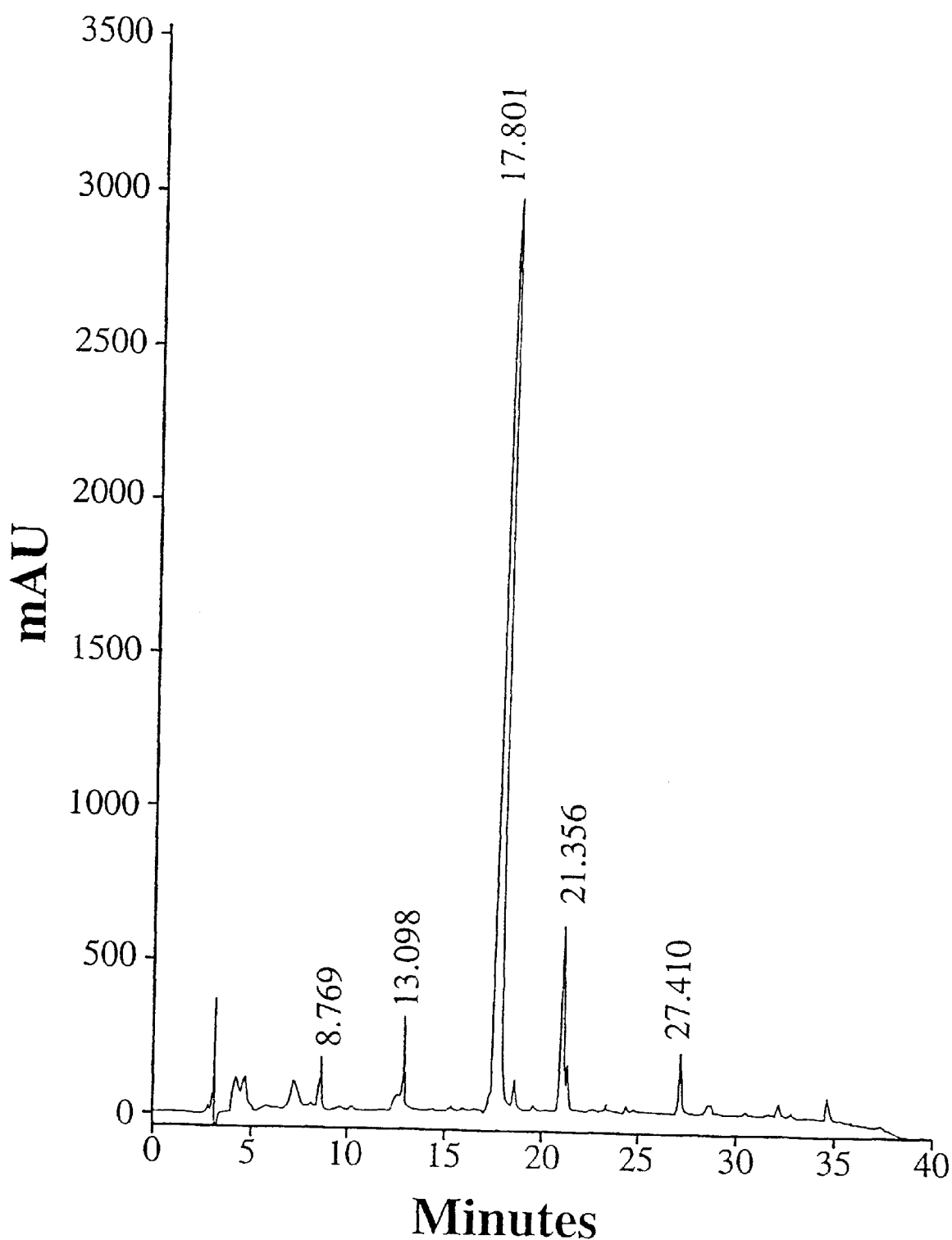
FIG. 4. HPLC chromatogram of the product obtained in example 55.

According to the present invention processes for the in situ generation of protected amino acid chlorides are provided utilizing an agent such as phosgene, diphosgene or triphosgene. In all the specific preferred embodiments presented herein the processes are exemplified utilizing solid phase peptide synthesis although these processes are also highly suitable to the synthesis of peptides in solution as known in the art. Moreover, the same processes can potentially be used to the coupling of other moieties to a peptide chain, including but not limited to the coupling of a carbohydrate moiety to a peptide chain, and for the methods of the multiple parallel peptide synthesis. The processes of the present invention are also highly suitable to the synthesis of complex peptide analogs such as bi- and tri- cyclic peptides, and synthesis of Cyclosporine analogs which comprise seven sterically hindered N-methyl amino acids. The processes are also suitable for formation of a urea bond in the sequence or in the bridge of cyclized peptides.

Abbreviations

Certain abbreviations are used herein to describe this invention and the manner of making and using it.

For instance, AA refers to amino acid; ACN refers to acetonitrile; Alloc refers to Allyloxycarbonyl; Boc refers to t-butoxycarbonyl; BOP refers to benzotriazole-1-yl-oxy-tris-(dimethylamino)phosphonium hexaflourophosphate; BTC refers to bis-(trichloromethyl)carbonate; DCM refers to dichloromethane; DIEA, diisopropylethylamine; DOTA refers to tetraazacyclodecanetetraacetic acid; DTPA, diethylenetriaminepentaacetic acid; eq refers to equivalents; Fmoc refers to fluorenylmethoxycarbonyl; Gln refers to Glutamine; HATU, O-(7-azabenzotriazol-1-yl)- 1,1,3,3-tetramethyluronium hexafluorophosphate; HOAt, 1-hydroxy-7-azabenzotriazole; HPPA, parahydroxy phenyl propionic acid; MBHA refers to methylbenzhydrilamine; Me refers to methyl; MPS refers to multiple parallel synthesis; NMP refers to N-methyl pyrollidone; Pmc refers to 2,2,5,7,8-Pentamethyl chroman-6-sulphonyl; PyBrOP, bromo-tris-pyrrolidino-phosphonium hexafluorophosphate; SPPS refers to solid phase peptide synthesis; t-Bu refers to t-butyl; TFA refers to trifluoroacetic acid; THF refers to tetrahydrofuran; TIS refers to triisopropylsilane; TOPPipU refers to 2-(2-Oxo-1(2H)-pyridyl)-1,1,3,3-bispentamethyleneuronium tetrafluoroborate; Trt refers to trityl; UNCA refers to urethane- protected N-carboxyanhydrides.

Amino acids

The amino acids used in this invention are those which are available commercially or are available by routine synthetic methods. Natural coded amino acids and their derivatives are represented by three-letter codes according to IUPAC conventions. When there is no indication, the L isomer was used. The D isomers are indicated by "D" before the residue abbreviation.

List of Non-coded amino acids: Abu refers to 2-aminobutyric acid, Aib refers to 2-amino-isobutyric acid, β-Ala refers to β-Alanine, Amb refers to 3 Amino methyl benzoic acid; ChxGly refers to cyclohexyl Glycine, Dab refers to Di amino butyric acid, GABA refers to gamma amino butyric acid, Hcys refer to homocystein, 1Nal refers to 1-naphthylalanine, 2Nal refers to 2-naphtylalanine, Nva refers to norvaline, (p-Cl)Phe refers to para chloro Phenylalanine, (p-NH₂)Phe refers to para amino Phenylalanine, (p-F)Phe refers to para fluoro Phenylalanine, (p-NO₂)Phe refers to para nitro Phenylalanine, Sar refers to Sarcosine, Thi refers to thienylalanine.

As used herein and in the claims, "blocked amino acid" denotes an amino acid in which a reactive group is protected by a specific blocking or protecting group which can be removed selectively, and may alternatively be denoted by the term "protected amino acid" as well known in the art.

As used herein "backbone cyclic peptide" denotes an analog of a linear peptide which contains at least one building unit that has been linked to form a bridge via the alpha nitrogen of the peptide backbone to another building unit, or to another amino acid in the sequence. A "building unit" indicates an N$^α$-ω-functionalized derivative of amino acid.

Building Units used in the synthesis of backbone cyclized peptides

A "building unit" indicates an N$^α$-ω-functionalized derivative of amino acid having the general Formula No. 1:

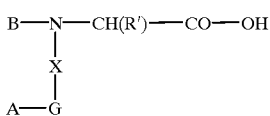

Formula No. 1 wherein X is a spacer group selected from the group consisting of alkylene, substituted alkylene, arylene, cycloalkylene and substituted cycloalkylene; R' is an amino acid side chain, optionally bound with a specific protecting group; B is a protecting group selected from the group consisting of alkyloxy, substituted alkyloxy, or aryl carbonyls; and G is a functional group selected from the group consisting of amines, thiols, alcohols, carboxylic acids and esters, aldehydes, alcohols and alkyl halides; and A is a specific protecting group of G.

Within the peptide sequence the building unit incorporated will have the following structure:

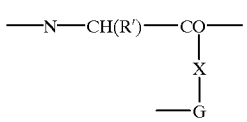

Formula No. 2 wherein X is a spacer group selected from the group consisting of alkylene, substituted alkylene, arylene, cycloalkylene and substituted cycloalkylene; R' is an amino acid side chain, optionally bound with a specific protecting group; and G is a functional group selected from the group consisting of amines, thiols, alcohols, carboxylic acids and esters, and alkyl halides; which is incorporated into the peptide sequence and subsequently selectively cyclized via the functional group G with one of the side chains of the amino acids in said peptide sequence or with another ω-functionalized amino acid derivative.

The building units are abbreviated by the three letter code of the corresponding modified amino acid followed by the type of reactive group (N for amine, C for carboxyl), and an indication of the number of spacing methylene groups. For example, GlyC2 describes a modified Gly residue with a carboxyl reactive group and a two carbon methylene spacer, and PheN3 designates a modified phenylalanine group with an amino reactive group and a three carbon methylene spacer.

The methodology for producing the building units is described in international patent applications published as WO 95/33765 and WO 98/04583 and in U.S. Pat. Nos. 5,723,575 5,811392; 5,883,293; 5,874,529 and 5,770,687, all of which are expressly incorporated herein by reference thereto as if set forth herein in their entirety.

General Procedures

For the majority of examples which follow, certain procedures were used throughout, which have therefore, for the sake of simplicity, been summarized herein under the heading general procedures.

General Procedure A: SPPS of model peptides 1 g Rink Amide methylbenzhydrilamine (MBHA) resin (0.55 mmol/g) were swelled for 1.5 hour in N-methyl pyrollidone (NMP) in a reaction vessel equipped with sintered glass bottom and placed on a shaker. The Fmoc protection was removed with 20% piperidine in NMP (twice fifteen minutes, 8 mL each). After washing with NMP (5 times, 8 mL for 2 minutes), the Fmoc removal was monitored by Kaiser test. A coupling cycle was carried out with Fmoc AA or Fmoc N-Me AA or Fmoc-building unit (3 equivalents) PyBrOP (3 equivalents) diisopropylethylamine (DIEA) (6 equivalents) in NMP (8 mL) for 1 hour at room temperature. Reaction completion was monitored by Kaiser test and the solvent was removed by filtration. The resin was washed with NMP (5 times, 8 mL 2 minutes). The Fmoc protecting group was removed as above. Coupling of Fmoc AA or Fmoc N-Me AA or Fmoc-building unit to AA-resin was performed as described above, using PyBrOP as coupling agent. Coupling of Fmoc AA or Fmoc N-Me AA or Fmoc-building unit to N-Me or building unit-resin was performed as described in General procedure B. Peptide elongation was performed by repeating the removal of the Fmoc protecting group and the coupling cycle described above. Final Fmoc deprotection was followed by washes (NMP 5 times, 8 mL 2 minutes and dichloromethane (DCM) 3 times, 8 mL 2 minutes). The peptidyl resin was dried in vacuum. Fast cleavage: a small amount of peptidyl resin was treated with 95% trifluouroacetic acid (TFA) containing 1% triisopropylsilane (TIS) and 4% $H_2O$. The solvents were removed by a stream of nitrogen and the residue was taken up in water:acetonitrile (ACN containing 0.1% TFA). After filtration the solution was injected to HPLC and/or to the mass-spectrometer.

General Procedure B: Coupling of Fmoc-AA's to AA peptidyl resin and to N-alkylated AA peptidyl resin using BTC Fmoc AA or Fmoc N-Me AA or Fmoc-building unit (5 eq, 0.275 mmol) and BTC (1.65 eq, 0.09 mmol) were dissolved in either tetrahydrofuran (THF), dioxane, diglyme, or in 1,3-dichloropropane to give 0.15 M solution, to which 2,4,6-collidine (14 eq, 0.75 mmol) was aded to give a white suspension. This suspension was poured into the N-Me AA or building unit's -peptidyl-resin prewashed with the appropriate solvent. The mixture was shaken at 50° C. for 1 hour and filtered. The peptidyl resin was washed with DCM, swelled with the appropriate reaction solvent, and the coupling repeated once more. In cases where coupling was performed with Fmoc-AA's to AA peptidyl resin, only 3 eq of Fmoc-AA's ,1 eq of BTC and 8 eq of 2,4,6-collidine were used in dioxane at room temp for 1 h.

General Procedure C: Coupling of Fmoc-AA or N-Me AA or building unit to a functionalized solid support Fmoc AA or Fmoc NMeAA or Fmoc-building unit chloride was prepared in situ as described in Procedure B. The suspension in dioxane was poured onto preactivated glass or onto hydroxymethylated polystyrene. The mixture was shaken at 50° C. for 1 hour and filtered. The derivatized support was washed with DCM. The degree of derivatization was determined by the Fmoc piperidine method.

General Procedure D: Derivatization of amino or hydroxy peptidyl resin

Acids such as 1,2,3,4-tetra-O-acetyl glucoronic acid, diethylentriaminepenta acetic acid (DTPA), tetraazacyclodecanetetraacetic acid ( DOTA) or parahydroxy phenyl propionic acid (HPPA) were converted to their corresponding acid chlorides using BTC as described in procedure B. The suspension was poured into amino or hydroxy peptidyl resin and heated 1 h. at 50° C. After filtration and wash, the derivatized peptidyl resin was cleaved and characterized as described in procedures A, G and H.

General Procedure E: SPPS of Backbone Cyclic Peptides—cyclization and cleavage

Peptidyl-resins that contain two building units were synthesized according to General procedures A & B. The Allyl/Alloc protecting groups were removed by reaction with Tetrakis/triphenylphosphine)-palladium, acetic acid 5% and N-methylmorpholine 2.5% in DCM under argon, for 1.5 hours at room temperature. The peptide resin was washed with chloroform followed by NMP. Cyclization was carried out in NMP with PyBOP (3 equivalents) and DIEA (6 equivalents) for 1 hour at room temperature. After washings with NMP the cyclization was repeated. The backbone cyclic peptide was deprotected and cleaved from the resin by treatment with 10 mL of TFA 94%, water 2.5%, TIS 1% and ethanedithiol 2.5% at 0° C. under argon for 0.5 hour and at room temperature for 1–3 hours. The resin was removed by filtration and washed with additional amount of TFA, the combined solution evaporated by a nitrogen stream to give an oil which upon treatment with cold ether (40 mL) solidified. The ether removed after centrifugation and the solid dried in high vacuum overnight to give the crude peptide.

General Procedure F: Cyclization of peptides containing two N-building units using BTC Peptidyl-resins that contain two N-building units were synthesized according to General procedures A, B and E. Cyclization was carried out in dioxane with BTC (0.33 eq) at room temp' for 1 h. Chemical procedures and characterization were done as described in General Procedure E, G and H.

General Procedure G: HPLC analysis of crude peptides

A sample of the crude peptides was dissolved in solvent A (water+0. 1% TFA) and injected into the HPLC machine (column C18 250×4 mm, flow 1 mL/minute). Eluent solvent A and B (ACN, 0.1% TFA). Hydrophobic peptides were eluted using linear gradient from 90% to 10% A in 35 minutes. Hydrophilic peptides were eluted using linear gradient from 100% to 10% A in 35 minutes. Peptides were detected by an online UV detector set at 214 nm.

General Procedure H: Mass spectral analysis of peptides

Crude peptides or fractions collected from the HPLC were analyzed by quadrupole or ion trap mass spectrometers.

The invention will be exemplified with regard to particular peptides and peptidomimetic compounds. These examples are to be construed in a non-limitative fashion, and it is understood that the invention is not limited by the scope of the examples, but rather by the scope of the claims which follow the specification.

EXAMPLES

Carboxylic acid chlorides are most conveniently prepared when BTC is reacted with carboxylic acids in an solvent inert to BTC at temperatures ranging from slightly above room temperature to reflux temperature, preferably in the presence of DMF or tertiary amines as catalysts. It is of importance that the solvent used be inert to BTC in order to obtain the desired synthetic results.

With that in mind and the fact that in the case of the pre-prepared Fmoc-AA's chlorides best conversions were obtained by heating in NMP, our preliminary studies with BTC were conducted under the following conditions: Fmoc-AA's (3 eq) and BTC (1.2 eq) were reacted in NMP followed by DIEA (12 eq) addition. After half an hour at room temperature, the activated AA's were poured into the peptide resin which was swelled at 65° C. for 1 h. Double coupling under these conditions gave the desired peptides but unfortunately with the loss of stereochemistry. Changing the base to the weaker sterically hindered 2,4,6-collidine did not improve the coupling stereointegrity significantly, as shown in Table 1.

It is concluded that the solvent NMP while being very efficient in general procedures of solid phase peptide synthesis as are well known in the art is not a suitable reagent for BTC mediated couplings.

TABLE 1

Summary of difficult couplings using BTClNMP at 65° C.

| No. | Substrate | R.T. (min) | Product | % Conversion (a) | Product Mass Calc. | Found | R.T. (min)(b) | Ratio of isomers(c) |
|---|---|---|---|---|---|---|---|---|
| 1 | AlaN3-Thr-Rink | 24.3 | Arg-Val-AlaN3-Thr-NH$_2$ | 100 | 585.41 | 586.83 | 20.42 + 20.81 | 1:9 |
| 2 | AlaN3-Thr-Rink | 24.3 | Arg-Phe-AlaN3-Thr-NH$_2$ | 100 | 633.41 | 634.86 | 24.10 + 25.92 | 1:1 |
| 3 | AlaC3-Thr-Rink | 6.20 | Phe-AlaC3-Thr-NH$_2$ | 100 | 462.29 | 463.1 | 14.23 + 14.65 | 1:3 |
| 4 | AlaC3-Thr-Rink | 6.20 | Leu-AlaC3-Thr-NH$_2$ | 100 | 428.31 | 429.1 | 12.99 + 13.33 | 1:5 |
| 5 | ValC3-Thr-Rink | 7.21 | Phe-ValC3-Thr-NH$_2$ | 100 | 490.32 | 491.1 | 17.04 + 17.42 | 9:1 |
| 6 | ValC3-Thr-Rink | 7.21 | Leu-ValC3-Thr-NH$_2$ | 100 | 456.34 | 457.1 | 16.04 + 16.31 | 1:20 |
| 7 | Leu3-Thr-Rink | 9.45 | Phe-LeuC3-Thr-NH$_2$ | 95 | 504.34 | 505.1 | 19.70 + 20.09 | 1:3 |
| 8 | Leu3-Thr-Rink | 9.45 | Leu-LeuC3-Thr-NH$_2$ | 90 | 470.36 | 471.1 | 18.79 | one isomer |
| 9 | ValN3-Trp-Rink | 14.91 | Phe-ValN3-Trp-NH$_2$ | 20 | 590.06 | 591.3 | 19.87 | one isomer |
| 10 | ValN3-Trp-Rink | 14.91 | Leu-ValN3-Trp-NH$_2$ | 20 | 556.39 | 557.2 | 19.72 | one isomer |

In entry 1-2, DIEA was used as base. R.T of substrate is for the Fmoc-protected derivative.

Entries 3–10 were performed in MPS format in 5.5 mM scale with collidine as base.

(a)Based on integration of area under the curve obtained from HPLC analysis.

(b)Analyzed according to general procedure G for hydrophobic peptides.

(c)Which have identical mass but different retention times.

Scheme 2
Proposed mechanism for coupling by BTC in NMP

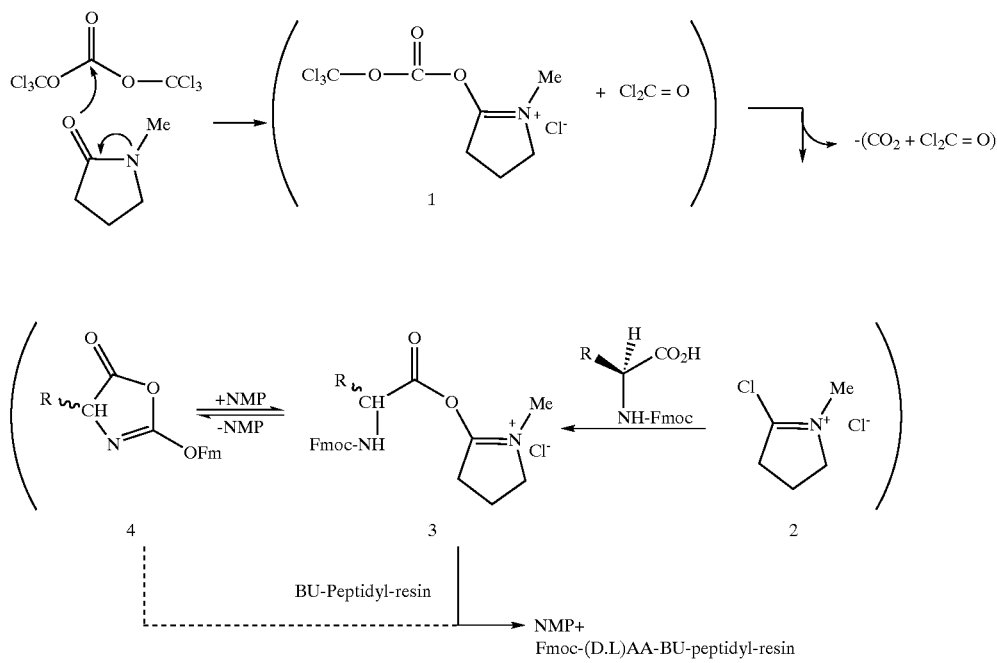

To explain the racemization of Fmoc AA's during their efficient BTC mediated coupling to building unit-peptidyl-resins in NMP we suggest a mechanism (Scheme 2) in which excess NMP reacts with BTC to form 1 which by losing phosgene and CO$_2$ furnished Vilsmayer-type intermediate 2. Addition of the optically pure Fmoc-AA to the chloroiminium ion 2, and elimination of the chloride, yields active ester 3, which couples to the peptide resin. On the other hand, N-alkoxycarbonyl protected amino active ester 3 under base catalysis is known to transform to oxazolone 4 which is ready racemizes. Further experiments with sterically hindered, polar amino acids, bearing protected side chains gave insufficient results as shown in Table 2.

TABLE 2

Summary of experiments using BTC/NMP with polar amino acids

| No. | Fmoc-AA | Substrate | % Conversion | Product Mass Calc. | Found | R.T. (min) (d) |
|---|---|---|---|---|---|---|
| 11 | Arg (Pmc) | AlaC3-Thr-Rink | 30(a)–100(b) | 471.23 | 472.3 | 8.07 |
| 12 | Glu (tBu) | LeuC3-Thr-Rink | 10(a)–50(b) | 486.32 | 487.0 | 14.60 |
| 13 | Glu (tBu) | AlaC3-Thr-Rink | 30(c) | 444.27 | 445.8 | 9.50 |
| 14 | Gln (Trt) | AlaC3-Thr-Rink | 30(c) | 443.28 | 444.9 | 8.52 |
| 15 | Met | AlaC3-Thr-Rink | 20(c) | 446.27 | 447.9 | 13.08 |

TABLE 2-continued

Summary of experiments using BTC/NMP with polar amino acids

| No. | Fmoc-AA | Substrate | % Conversion | Product Mass Calc. | Found | R.T. (min) (d) |
|---|---|---|---|---|---|---|
| 16 | Trp (Boc) | AlaC3-Thr-Rink | 80(c) | 501.3 | 502.8 | 16.22 |

(a)After 1 h. at 75° C.;
(b)After 3 coupling cycles at 65° C.;
(c)After 2 coupling cycles at 65° C.;
(d)Analyzed according to the general procedure G for hydrophobic peptides.

The total failure of these amino acids and a large variety of other polar and aromatic Fmoc AA's to couple to the more hindered building units-peptidyl-resin, and also the fact that no reaction was obtained with Fmoc-Asn(Trt) and Fmoc-His(Trt) even with Ala-building unit-peptidyl-resin in NMP, required changing to a solvent inert to the reaction. Indeed, double coupling of Fmoc-Val and Fmoc-Ile to N$^\alpha$-(ω-carballyloxypropyl)-Ala (denoted AlaC3) and N$^\alpha$-(ω-carballyloxypropyl)-Leu (denoted LeuC3) -peptidyl-resins using BTC in THF for only 1 h. at 50° C. afforded the desired peptide in 100% conversion and with no detectable racemization. These results prompted us to undertake a wide synthetic effort which includes the coupling of all proteinogenic Fmoc-AA's (except Gly) to a large variety of building units-peptidyl-resins and also to N-Me-Ala and to N-Me-Phe-peptidyl-resins, where the size and sequence of the peptidyl moiety varies. The results are shown in Table 3 and Table 4.

TABLE 3

Summary of difficult coupling using BTC/THF, Dioxane, Diglyme or DCP

| No | Fmoc AA | Substrate | % Convers | Product Mass Calc. | Found | R.T. (min) |
|---|---|---|---|---|---|---|
| 17 | Ala | AlaN3-Rink | 100 A,B | 502.9$^A$ | 503.9$^A$ | 9.45$^{AX}$ |
|  |  |  |  | 583.4$^B$ | 584.4$^B$ | 11.65$^{BY}$ |
| 18 | Ala | AlaC2-Rink | 100 | 554.1 | 555.1 | 13.92$^Y$ |
| 19 | Ala | AlaC3-Rink | 100 A,B | 682.4$^A$ | 683.4$^A$ | 14.13$^{AY}$ |
|  |  |  |  | 633.5$^B$ | 634.5$^B$ | 13.37$^{BY}$ |
| 20 | Ala | AlaN2-Rink | 100 A,B | 569.3$^A$ | 570.3$^A$ | 11.01$^{AY}$ |
|  |  |  |  | 488.16$^B$ | 489.2$^B$ | 9.79$^{BX}$ |
| 21 | Ala | LeuN4-Ser-Rink | 90 | 443.15 | 444.9 | 13.30$^X$ |
| 22 | D-Ala | AlaN2-Peptide-Rink | 100 | 682.4 | 683.4 | 14.13$^Y$ |
| 23 | Arg(Pmc) | PheC2-Thr-Rink | 94 | 533.33 | 534.3 | 24.38$^Y$ |
| 24 | Asp(tBu) | LysC3-Thr-Rink | 100 | 487.31 | 488.9 | 15.67$^Y$ |
| 25 | Cys(Trt) | ValC3-Thr-Rink | 100 | 446.26 | 447.1 | 26.39$^Y$ |
| 26 | Glu(tBu) | LysC3-Thr-Rink | 70 | 501.33 | 502.2 | 16.81$^Y$ |
| 27 | Gln (Trt) | PheC2-Thr-Rink | 100 | 505.28 | 506.2 | 28.97$^Y$ |
| 28 | Gln(Trt) | ValC3-Thr-Rink | 82 | 471.2 | 472.2 | 22.95$^Y$ |
| 29 | Gln(Trt) | LeuN4-Ser-Rink | 100 | 500.9 | 501.9 | 12.34$^X$ |
| 30 | D-Leu | LeuN4-Ser-Rink | 100 | 486.0 | 487.0 | 17.70$^X$ |
| 31 | Leu | PheN2-Gln-Rink | 100 | 1081.7 | 1082.7 | 17.31$^X$ |
| 32 | Leu | LysC3-Thr-Rink | 100 | 485.37 | 486.2 | 22.43$^Y$ |
| 33 | Ile | LeuC3-Thr-Rink | 80 | 470.36 | 472.0 | 18.97$^X$ |
| 34 | Lys(Boc) | LeuN4-Ser-Rink | 100 | 501.0 | 502.0 | 11.26$^Y$ |
| 35 | Lys(Boc) | PheC2-Thr-Rink | 100 | 505.32 | 506.1 | 24.53$^Y$ |
| 36 | Lys(Boc) | ValC3-Thr-Rink | 56 | 472.2 | 473.0 | 22.12$^Y$ |
| 37 | Lys(Boc) | PheN2-Rink | 100 | 1002.4 | 1003.4 | 23.21$^X$ |
| 38 | D-Lys(Boc) | PheN2-Rink | 100 | 1002.4 | 1003.4 | 23.02$^X$ |
| 39 | D-Lys(Boc) | PheN2-Rink | 100 | 968.4 | 969.5 | 22.71$^X$ |
| 40 | Met | LeuN4-Ser-Rink | 100 | 503.15 | 504.9 | 16.08$^X$ |
| 41 | Phe | AlaC3-Peptide-Rink | 100 | 1716.0 | 1716.8 | 14.76$^X$ |
| 42 | Phe | AlaN2-Rink | 100 | 678.49 | 679.9 | 20.45$^X$ |
| 43 | Phe | N-MePhe-N-MePhe-Rink | 100 | 528.2 | 529.9 | 22.06$^Y$ |
| 44 | PheCl | N-MeAla-Ala-AlaN2-Rink | 100 | 616.8 | 617.8 | 16.25$^X$ |
| 45 | PheC2 | N-MeAla-Ala-AlaN3-Rink | 100 | 502.9 | 503.9 | 9.45$^X$ |
| 46 | PheC2 | N-MeAla-Ala-AlaN2-Rink | 100 | 488.2 | 489.2 | 9.79$^X$ |
| 47 | N-MePhe | N-MePhe-Rink | 100 | 528.2 | 529.9 | 22.06$^Y$ |
| 48 | N-MePhe | N-MePhe-N-MePhe-Rink | 100 | 500.18 | 501.2 | 18.52$^X$ |
| 49 | Pro | ValC3-Thr-Rink | 100 | 440.31 | 441.2 | 25.95$^Y$ |
| 50 | Ser(tBu) | LysC3-Thr-Rink | 100 | 459.32 | 460.1 | 15.61$^Y$ |
| 51 | Thr(tBu) | AlaC2-Peptide-Rink | 100 | 1587.4 | 1588.7 | 19.25$^Y$ |
| 52 | Thr(tBu) | AlaC3-Peptide-Rink | 100 | 1601.4 | 1602.7 | 19.67$^Y$ |
| 53 | Thr(tBu) | ValC3-Thr-Rink | 53 | 444.3 | 445.1 | 24.35$^Y$ |
| 54 | Trp(Boc) | ValN3-Trp-Rink | 100 | 629.38 | 630.2 | 20.01$^X$ |
| 55 | Trp(Boc) | ValC3-Thr-Rink | 100 | 529.33 | 530.1 | 17.80$^X$ |
| 56 | Tyr(tBu) | LeuN3-Amb-Ala-Arg-Rink | 100 | 1322.6 | 1323.6 | 19.05$^X$ |
| 57 | D-Tyr(tBu) | AlaN3-Rink | 100 | 1716.0 | 1716.8 | 14.76$^X$ |
| 58 | Val | AlaC3-Thr-Rink | 100 | 414.29 | 416.0 | 11.93$^X$ |
| 59 | Val | LysC3-Thr-Rink | 92 | 471.35 | 472.1 | 19.49$^Y$ |
| 60 | Val | ValC3-Thr-Rink | 66 | 442.32 | 443.1 | 14.94$^X$ |
| 61 | PheC3 | Thr-Rink | 100 | 391.23 | 392.9 | 10.64$^X$ |

Product mass data

In entries 17, 18, 19, 20, 22, 31, 37, 44, 45, 46, 57 data correspond to the cyclic peptides.

In entries 42, 51, 52, 56 data corresponds to the Allyl/Alloc protected peptides.

In entries 22, 41, 48, 51, 52 data correspond to the linear peptides.

In entries 43, 47 data correspond to the Ac-N tripeptide.
Peptide sequences
17$^A$) PheC2-NMeAla-Ala-AlaN3-NH$_2$;
17$^B$) GlyC1 -Ala-Lys-(D)Ala-Ala-AlaN3- NH$_2$;
18) Ala-Ala-Lys-(D)Ala-Ala-AlaC2-NH$_2$;
19$^A$) (D)Ala-AlaN2-Ala-Lys-(D)Ala-Ala-AlaC3-NH$_2$;
19$^B$) AlaN2-Ala-Lys-(D)Ala-Ala-AlaC3-NH$_2$;
20$^A$) GlyC1-Ala-Lys-(D)Ala-Ala-AlaN2-NH$_2$;
20$^B$) PheC2-N-MeAla-Ala-AlaN2-NH$_2$;
22) (D)Ala-AlaN2-Ala-Lys-(D)Ala-Ala-AlaC3- NH$_2$;
31) TrpC3-Ser-Glu-Tyr-Leu-PheN2-Gln-NH$_2$(SEQ ID NO:1);
37) PheC1-Phe-Phe-(D)Trp-(L)Lys-PheN2-NH$_2$ ;
38) PheC1-Phe-Phe-(D)Trp-(D)Lys-PheN2-NH$_2$ ;
39) PheC1-Phe-Leu-(D)Trp-(D)Lys-PheN2-NH$_2$;
41) Biotin-Trp-Arg-Lys-(D)Arg-Phe-AlaC3-NH$_2$;
42) PheC1-Ala-Phe-AlaN2-NH$_2$;
47) Phe-NMePhe-NMePhe-NH$_2$;
48) NMePhe-NMePhe-NMePhe-NH$_2$;
51) Thr-AlaC2-Ser-Glu-Asn-His-Leu-Arg-His-Ala-LeuN3-Ser-NH$_2$(SEQ ID NO:2);

52) Thr-AlaC3-Ser-Glu-Asn-His-Leu-Arg-His-Ala-LeuN3-Ser-NH$_2$(SEQ ID NO:3);

56) TrpC3-Ser-Glu-Tyr-LeuN3-Amb-Ala-Arg- NH$_2$(SEQ ID NO:4); and

57) Biotin-Trp-Arg-Lys-(D)Arg-Phe-AlaC3-Leu-Arg-(D)Tyr-AlaN3-NH$_2$.

HPLC analysis methods $^X$Analyzed according to the general procedure G for hydrophobic peptides.

$^Y$Analyzed according to the general procedure G for hydrophilic peptides.

As can be seen in Table 3 the conversion of most of the couplings were quantitative regardless of the incoming Fmoc-AAs, the structure of the building unit, the sequence and the size of the peptidyl moiety. In the following description the bold numbers in brackets denote the example numbers, as per table 3.

Three peptides (26, 36 and 53) gave below 70% conversion. It should be noticed that these couplings were not optimized.

Contrary to the pre-formed acid chloride method, where there was a major problem with the lability of the side chain protection groups, using the methods of the current invention the coupling of the following Fmoc-AAs gave substantially complete conversion: Arg(Pmc) (23), Asp(t-Bu) (24), Cys(Trt) (25), Lys(Boc) (34, 35), Ser(t-Bu) (50), Thr(t-Bu) (51, 52), Trp(Boc) (54) and Tyr(t-Bu) (56, 57). Since the side-chain Boc protecting group is easily removed by acids, we have monitored its stability by the Keiser test during the BTC mediated coupling of Fmoc-Lys(Boc) (34, 39). During all these couplings the Keiser test was negative and the desired backbone cyclic peptides were obtained in excellent yields without side products in the crude. From these results it can be concluded that coupling with BTC under the conditions described above does not remove sensitive side chain protecting groups normally used in solid phase peptide synthesis with Fmoc chemistry.

We have shown that most of the Fmoc-AA chlorides do not racemize during couplings to building unit-peptidyl-resin in various solvents with or without collidine as base. The assessment of the degree of racemization during couplings mediated by BTC in solvent inert to this reaction is based on the following results: (a) as shown in Table 1 when racemization occurs, two peaks with identical mass were found by HPLC. In all the peptides shown in Table 3, including those peptides that gave low yields (21, 23, 26, 28, 33, 36, 53, 58, 59) only the major peak gave the desired mass. (b) coupling of Fmoc-Lys(Boc) and Fmoc-D-Lys (Boc) to PheN2 building unit-resin, further assembly of the peptides, Allyl/Alloc deprotection, cyclization and removal from the resin yielded two diastereomeric backbone cyclic peptides (37, 38) in quantitative conversion. The HPLC profile of each individual crude diastereomer showed a single distinct peak with the same mass and different retention times from one another. Moreover, co-injection to Capillary Electrophoresis of the two diasteromers 37 and 38 gave two separate peaks. The lack of racemization during the coupling of Fmoc-AAs chlorides to building unit-peptidyl-resin is due to the high reactivity of acid chlorides to the nucleophilic acyl substitution compared to the slower oxazolon formation. Since the BTC mediated coupling in solvents inert to this reaction proceeds via in-situ acid chloride formation, it is not surprising that generally this coupling proceeds without racemization.

In order to find the limitations of BTC to promote difficult couplings we synthesized peptides 44–46 in which various Phe building units were coupled to N-Me-Ala-peptidyl-resin. In addition, in peptide 43 Fmoc-Phe was coupled to N-Me-Phe-N-Me-Phe-resin and in peptide 48 Fmoc-N-Me-Phe was coupled to N-Me-Phe-N-Me-Phe-resin. All these repetitive couplings proceeded in short time with quantitative conversion and leads to the conclusion that BTC is the reagent of choice to promote difficult couplings in SPPS.

In most of the peptides presented in Table 3, the coupling was performed on di-peptidyl building unit-resin. In order to test the capability of BTC to effect couplings to building unit attached in other positions along the peptide chain, coupling was performed in positions 4–6 and 11 (peptides 56, 41, 22, 51 and 52, respectively).

Table 4 depicts an overview of the peptides synthesized by BTC coupling and correlates the type of the incoming building unit with the position of coupling along the peptide chain. While couplings to positions 4–6 proceeded under the normal conditions, coupling to position 11 needed six cycles to achieve quantitative conversion.

TABLE 4

Summary of Difficult Coupling Reactions Using the BTC Method

| Building Unit | Amino acid coupled to Building Unit | | | | | | | | | | | | | | |
|---|---|---|---|---|---|---|---|---|---|---|---|---|---|---|---|
| | Ala | DAla | DLeu | Ile | Leu | Val | Gln | Lys | DLys | Phg | Phe | PheC1 | PheC2 | Met | Ser |
| AlaN3 | 1 | | | 4a | | | | | | | | | | | |
| AlaC2 | 1 | | | | | | | | | | | | | | |
| AlaC3 | 1 | | | | | 2 | | | | | 5 | | 8 | | |
| AlaC4 | | | | | 1 | | | | | 1 | 6 | | | | |
| AlaC5 | | | | | | | | | | | | | | | |
| AlaN2 | 1,2 | 6 | | | | 1,2 | | | | | 1 | | | | |
| PheN2 | | | | 7b | 1,2 | | 5a | | 1 | | | | | | |
| PheC4 | | | | | | | | | | | 1 | | | | |
| PheC2 | | | | 3 | | 2 | 2 | | | | | | | | |
| PheN3 | | | | | | | | | | | | | | | |
| LeuN4 | 3 | | 2 | | | 2 | 2 | | | | | | | 2 | |
| LeuN3 | 2 | | | | | | | | | | | | | | |
| LeuC3 | | | | 2 | | | | | | | | | | | |
| LysN3 | 2 | | | | | | | | | | | | | | |
| LysC3 | | | | 2 | 2 | 2 | | | | | | | | | 2 |
| LysC4 | | | | | | | | | | | 6 | | | | |
| ValC3 | | | | | 2 | 2 | 2 | | | | | | | | |
| ValN3 | | | | | | | 5a | | | | 2 | | | | |

TABLE 4-continued

Summary of Difficult Coupling Reactions Using the BTC Method

| | | | | | | | | | | | | | | |
|---|---|---|---|---|---|---|---|---|---|---|---|---|---|---|
| NMePhe | | | | | | | | | | | 2 | | | |
| NMeAla | | | | | | | | | | | | 3 | 3 | |
| GlyC3 | | | | | | | | | | | 1 | | | |
| NMeGly | | | | | | | | | | | | | | |
| DTrpN2 | | | | | | | | | | | | | | |

| Building Unit | Amino acid coupled to Building Unit | | | | | | | | | | | | | |
|---|---|---|---|---|---|---|---|---|---|---|---|---|---|---|
| | Arg | Asp | Asn | His | Thr | NMePhe | Tyr | DTyr | Pro | Trp | Cys | Glu | GlyC2 | NMeGly | GABA |
| AlaNe | | | | | | | | 1 | | | | | | | |
| AlaC2 | | | | | 11(6), 2 | | | | | | | | | 5 | |
| AlaC3 | | | | | 11(6) | | 9 | | | | | | | | |
| AlaC4 | | | | | | | | | | | | 12 | | | |
| AlaC5 | | 2 | | | | | | | | | | | | | |
| AlaN2 | | | | | | | | | | | | 3,5(4) | 7 | 1 | |
| PhcN2 | | | | | | | | | | | | | | | |
| PheC4 | | | | | 11 | | | | | | | | | | |
| PheC2 | 2 | | | ** | | | | | | | | | 9 | | |
| PheN3 | | | | | | | | | | | 1 | | | | |
| LeuN4 | | 1 | | | | | | | | | | | | | |
| LeuN3 | | | | | | 4 | | | | | | | | | |
| LeuC3 | | | | | | | | | | | | | | | |
| LysN3 | | | | | | | | | | | | | | | |
| LysC3 | | 2 | | | | | | | | | | | 2 | | |
| LysC4 | | | | | | | | | | | | | | | |
| ValC3 | # | | nr | | 2*** | | | 2 | | 2 | 2 | | | | |
| ValN3 | | | | | | | | | | 2 | | | | | |
| MePhe | | | | | 2 | 1 and 2 | | | | | | | | | 7 |
| MeAla | | | | | | | | | | | | | | | |
| GlyC3 | | | | | | 1 | | | | | | | | | |
| MeGly | | | | | | | | | | | | | | 2,3,4 | |
| DTrpN2 | 1 | | | | | | | | | | | | | | |

Footnotes to Table 4:
The numbers in the table indicate the building unit position (from C-terminal) to which the AA was coupled in >80% conversion based on HPLC and confirmed by MS
*Double coupling with 5 eq AA, 1.5 eq BTC(0.33eq per AA), 14 eq Collidine in inert solvent (0.14M) at 500C for 1h
**Only 20% conversion with epimerization
nr = No reaction
() = number of coupling cycles
= 5–10%
a preactivation with BTSA
b preactivation of the building unit-peptidyl resin with BTSA, 4–7 coupling cycels and addition of AgCN The use of BTC for the couplings of Fmoc-His(Trt) and FmocAsn(Trt) were unsuccessful. The coupling of Fmoc-His(Trt) gave only 20% conversion with total racemization and there was no coupling with Fmoc-Asn(Trt).

Example 62
Synthesis of bicvclic peptide PTR 3205

Two grams of Rink Amide (MBHA resin, NOVA, 0.46 mmol/gram) were swelled over night in NMP in a reactor equipped with a sintered glass bottom, attached to a shaker. Fmoc was removed from the resin using 25% Piperidine in NMP (16 ml) twice for 15 min. After careful wash, seven times with NMP (10–15 ml), for 2 min each, coupling of Phe-N3 was accomplished using Fmoc-Phe-N3-OH (3 eq, 2.76 mmol, 1.46 gram) dissolved in NMP (16 ml) and activated with PyBroP (2.76 mmol, 1.28 gram) and DIEA (6 eq, 5.52 mmol, 0.95 ml) for 4 min at room temperature and then transferred to the reactor for coupling for 1 h at room temperature. Following coupling the peptide-resin was washed with NMP (10–15 ml) seven times for 2 min each. Reaction completion was monitored by qualitative Kaiser test. Fmoc removal and wash was carried out as described above followed by wash with THF (10–15 ml) three times for 2 min each and Fmoc-Cys(Acm)-OH (5 eq, 4.6 mmol, 1.9 gram) was coupled to the building unit-peptidyl resin using bis-(trichloromethyl)carbonate (1.65 eq, 1.518 mmol, 0.45 gram) and collidine (14 eq, 12.88 mmol, 1.7 ml) in THF (30–35 ml, to give 0.14 M mixture) at 50° C. for 1 h. and this coupling procedure was repeated. Assembly of Thr, Lys, (D)Trp, Phe, Cys and PheC3 was accomplished by coupling cycles (monitored by qualitative Kaiser test) using Fmoc-Thr(tBu)-OH, Fmoc-Lys(Boc)-OH, Fmoc-(D)Trp(Boc)-OH, Fmoc-Phe-OH, Fmoc-Cys(Acm)-OH and Fmoc-PheC3-OH respectively, in each coupling cycle the amino acid was dissolved in NMP and was activated with PyBroP and DIEA, following coupling the peptide-resin was washed than Fmoc removed followed by extensive wash with NMP, as described above for the first coupling. At the end of the assembly the peptidyl-resin underwent allyl/alloc deprotection under the following conditions: the peptidyl resin was washed with DCM (10–15 ml) three times for 2 min each and with a mixture of DCM-AcOH-NMM (92.5%, 5%, 2.5% respectively) three times for 2 min each. 3 gram of Pd(P(Ph)$_3$)$_4$ were dissolved in the above mixture (80 ml) and the yellow suspension obtained was transferred to the reactor and the mixture with the peptidyl-resin underwent degassing (by babbling Argon through the reactor's sintered glass bottom) and then vigorously shacked for 2 h in the dark. The peptidyl-resin washed with DCM, CHCl$_3$ and NMP (a total of 15 washes 2 min each). Cyclization using PyBOP (3 eq, 2.76 mmol, 1.436 gram) and DIEA (6 eq, 5.52 mrnmol, 0.95 ml) in NMP (20 ml) at room temperature for 1 h and then second cyclization over night (under same conditions) took place. The peptidyl resin was washed with NMP followed by wash with DMF-water (15 ml, 4:1) three times for 2 min each. I$_2$ solution (5 eq, 4.6 mmol, 1.16 gram) in DMF-water (23 ml, 4:1) was added to the peptidyl-resin which was shacked at room temperature for 40 min to afford Cys-Cys cyclization. The peptidyl resin was filtered and washed extensively with DMF/water, DMF, NMP, DCM, CHCl$_3$ and also with 2% ascorbic acid in DMF. After final Fmoc deprotection and wash as above and also wash with MeOH, followed by drying the peptidyl resin under vacuum for 20 min the peptide was cleaved from the resin using 95% TFA, 2.5% TIS and 2.5% water in a total of 30 ml cocktail mixture for 30 min at 0° C. under Argon and then 1.5 h at room temperature. The solution was filtered through extract filter into polypropylene tube, the resin was washed with 5–6 ml cocktail and 4–5 ml TFA, the solution was evaporated by N$_2$ stream to give oily residue which on treatment with cold Et$_2$O solidify. Centrifugation and decantation of the Et$_2$O layer and treatment with additional portion of cold Et$_2$O followed by centrifugation and decantation and drying the white solid under vacuum over night gave crude PTR 3205 (0.388 gram) having the following structure:

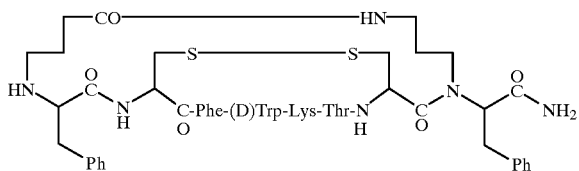

Example 63
Synthesis of tricyclic peptide PTR 3227

PTR 3227 is a tricyclic backbone cyclic peptide having the following structure:

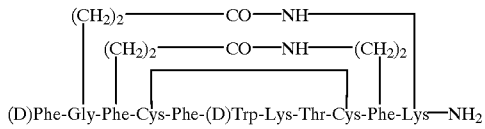

Figure 5:
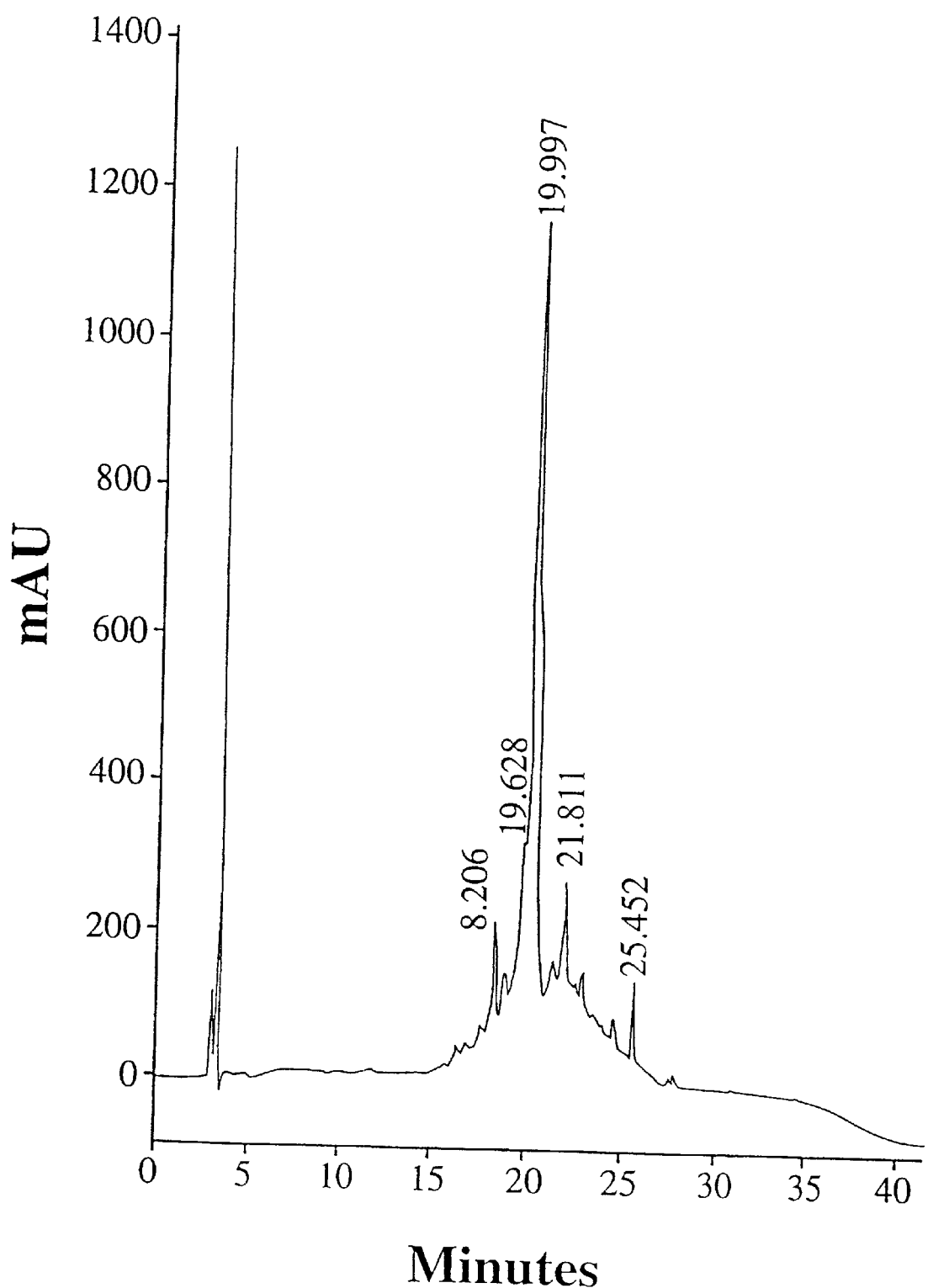
FIG. 5. HPLC chromatogram of PTR 3227 obtained in example 63.

In this compound, one bridge connects a building unit (Gly-C2) to the side chain of Lys residue, a second bridge connects two building units (Phe-N2 and Phe-C2), and the third is a disulfide bridge formed between two Cys residues. The synthesis procedure of this analog is now described:

1 gram Rink Amide (MBHA resin, Novabiochem, 0.46 mmol/gr) was swelled over-night in NMP in a reactor equipped with a sintered glass bottom, attached to a shaker. Fmoc was removed from the resin using 25% Piperidine in NMP (16 ml) twice for 15 min. After careful wash, seven times with NMP (10–15 ml), for 2 min each, coupling of Lys(Dde) was accomplished using Fmoc- Lys(Dde)-OH (3 eq, 1.38 mmol, 0.735 gram) dissolved in NMP (8 ml) and activated with PyBroP (1.38 mmol, 0.64 gram) and DIEA (6 eq, 2.76 mmol, 0.47 ml) for 4 min at room temperature and then transferred to the reactor for coupling for 1 h at rt. Following coupling the peptide-resin was washed with NMP (10–15 ml) seven times for 2 min each. Reaction completion was monitored by qualitative Kaiser test. Fmoc removal and wash was carried out followed by coupling of Fmoc-PheN2-OH (3 eq, 1.38 mmol, 0.71 gram) as described above. Following coupling Fmoc removal and wash with NMP the peptide-resin was washed with THF (10–15 ml) three times for 2 min each and Fmoc-Cys(Acm)-OH (5 eq, 2.3 mmol, 0.95 gram) was coupled to the BU-peptidyl-resin using BTC (1.65 eq, 0.759 mmol, 0.225 gram) and collidine (14 eq, 6.44 mmol, 0.85 ml) in THF (16 ml, to give 0.14 M mixture) at 50° C. for 1 h. This difficult coupling procedure was repeated once more. Assembly of Thr, Lys, (D)Trp, Phe, Cys and PheC2 was accomplished by coupling cycles (monitored by qualitative Kaiser test) using Fmoc-Thr(tBu)-OH, Fmoc-Lys(Boc)-OH, Fmoc-(D)Trp(Boc)-OH, Fmoc-Phe-OH, Fmoc-Cys(Acm)-OH and Fmoc-PheC2-OH respectively, in each coupling cycle the amino acid was dissolved in NMP and was activated with PyBroP and DIEA, following coupling the peptide-resin was washed than Fmoc removed followed by extensive wash with NMP, as described above for the first coupling. After the assembly of PheC2 the peptidyl-resin underwent allyl/alloc deprotection under the following conditions: the peptidyl resin was washed with DCM (10–15 ml) three times for 2 min each and with a mixture of DCM-AcOH-NMM (92.5%, 5%, 2.5% respectively) three times for 2 min each. 1.5 gram of Pd(P(Ph)$_3$)$_4$ were dissolved in the above mixture (40 ml) and the yellow suspension obtained was transferred to the reactor and the mixture with the peptidyl-resin underwent degassing (by babbling Argon gas through the reactor's sintered glass bottom) and then vigorously shacked for 2 h in the dark. The peptidyl-resin was washed with DCM, CHCl$_3$ and NMP (a total of 15 washes 2 min each). Cyclization using PyBOP (3 eq, 1.38 mmol, 0.72 gram) and DIEA (6 eq, 2.76 mmol, 0.475 ml) in NMP (10 ml) at room temperature for 1 h and then second cyclization over night (under same conditions) took place. Fmoc-deprotection was then preformed as described above followed by NMP wash, then Fmoc-GlyC2-OH was coupled to the cyclic peptide using 5 eq of the BU (2.3 mmol, 0.94 gram), BTC (1.65 eq, 0.759 mmol, 0.225 gram) and collidine (14 eq, 6.44 mmol, 0.85 ml) in THF (16 ml, to give 0.14 M mixture) at 50° C. for 1 h. and this difficult coupling procedure was repeated once more. Coupling of (D)-Phe to the decapeptide-resin was done using Boc-(D)-Phe-OH (4 eq, 1.84 mmol, 0.488 gram) and PyBrop (1.84 mmol, 0.857 gram) as coupling reagent and DIEA (8 eq, 3.68 mmol, 0.63 ml) as a base in DMF/DCM (1:1, 8 ml) once for 1.5 h. and second coupling cycle under same conditions for 2 h at room temperature. Next, followed wash selective removal of Dde from N$\epsilon$ side chain of the Lys (at position 1 from C-terminal) was done using 2% hydrazine in DMF (25 ml×3 min×3) at rt. after wash with DMF and NMP the peptidyl resin underwent allyl deprotedtion as described above using 0.75 gram of Pd(P(Ph)$_3$)$_4$, The peptidyl resin was washed with CHCl$_3$, DCM and NMP followed by cyclization with PyBOP as described above (Kaiser test was negative). Followed by wash with DMF-water (12.5 ml, 4:1) three times for 2 min each. I$_2$ solution (5 eq, 2.3 mmol, 0.583 gram) in DMF-water (12.5 ml, 4:1) was added to the peptidyl-resin which was shacked at room temperature for 40 min to afford Cys-Cys cyclization. The peptidyl resin was filtered and washed extensively with DMF/water, DMF, NMP, DCM, CHCl$_3$ and also with 2% ascorbic acid in DMF followed by DMF. After wash with DCM and MeOH, followed by drying the peptidyl resin under vacuum for 20 min the peptide was cleaved from the resin using 95% TFA, 2.5% TIS and 2.5% water in a total of 15 ml cocktail mixture for 30 min at 0° C. under Argon and then 1.5 h at room temperature. The solution was filtered through extract filter into polypropylene tube, the resin was washed with 5–6 ml cocktail and 4–5 ml TFA, the solution was evaporated by N$_2$ stream to give oily residue which on treatment with cold Et$_2$O solidify. Centrifugation and decantation of the Et$_2$O layer and treatment with additional portion of cold Et$_2$O followed by centrifugation and decantation and drying the with solid under vacuum over night gave crude PTR-3227 (72 mg, 10 %). The HPLC chromatogram of the crude peptide is represented in FIG. 5.

Example 64
Coupling of Galactose Derivative to a Backbone Cyclic Peptide to yield PTR 3229

Figure 6:
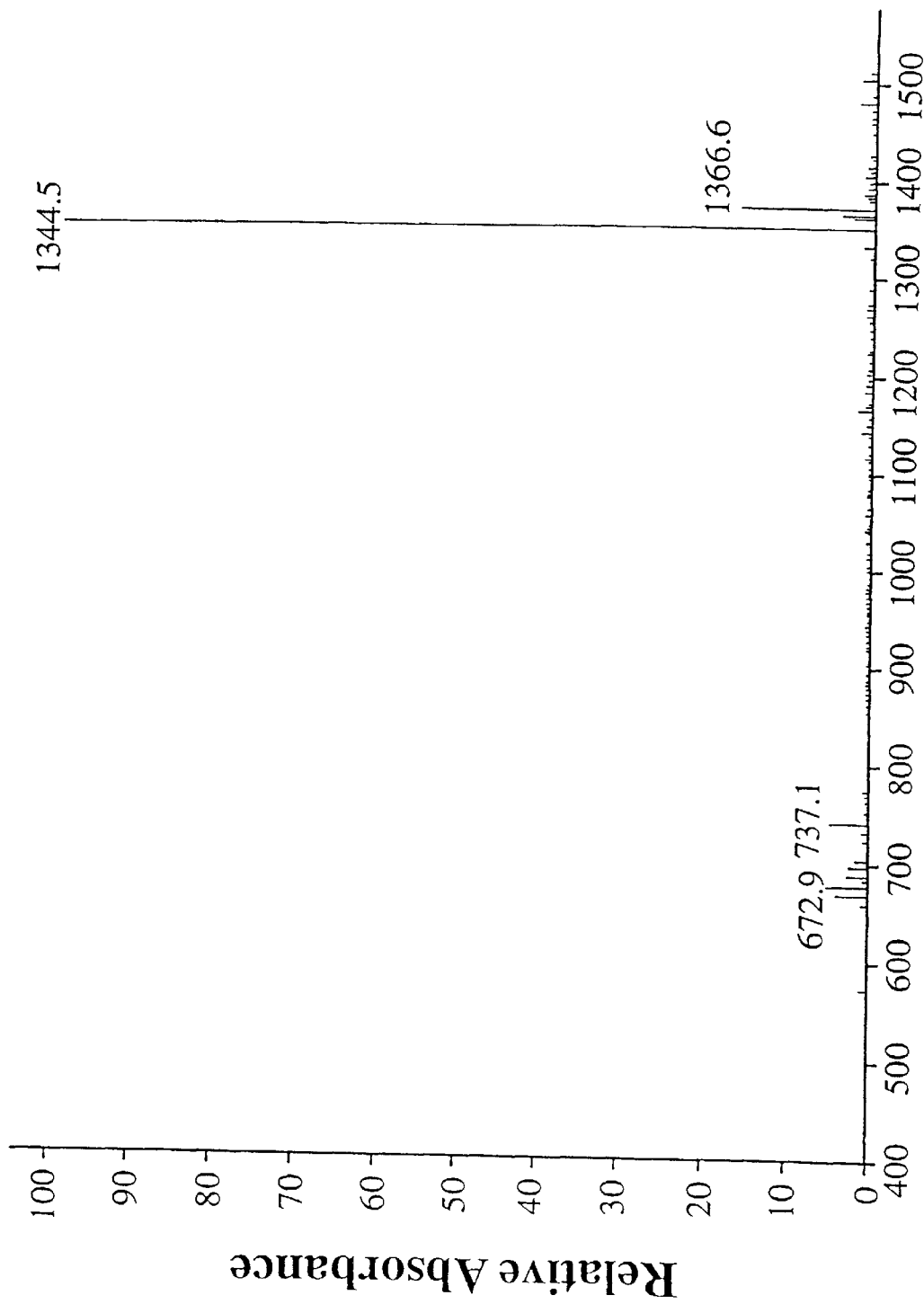
FIG. 6. Mass spectra analysis of PTR 3229 obtained in example 64.

Backbone cyclic peptide underwent Fmoc deprotection followed by washes with NMP and THF. A coupling cycle with 1,2:3,4-Di-O-isopropylidene D-galactopyranose (5 eq, 1.15 mmol, 0.3 gram) using 0.33 eq of BTC (0.379 mmol, 0.112 gram) as the coupling reagent and 14 eq of collidine (3.22 mmol, 0.425 ml) as a base in THF (15 ml) at rt was preformed for 1 h. After wash with DCM and MeOH the peptide was cleaved from the resin using TFA (95%/0), TIS (2.5%) and water (2.5%) in a total volume of 15 ml cocktail mixture for 1.5 h. at rt. After further work-up crude PTR-3229 (0.176 gram), having the sequence: Galactose-Dab-Phe-Trp-(D)Trp-Lys-Thr-Phe-Gly(C3)-NH$_2$, was obtained. This peptide analog comprises a bridge connecting the GlyC3 building unit and the Dab residue. The mass spectra analysis of the crude peptide are represented in FIG. 6.

Example 65
Formation of a urea bond using BTC

A. Formation of a urea bond in the bridge by coupling Ile (isocyanate derivative formed by BTC), to Lys-peptidyl resin to form the peptide analog PTR 3237 having the following structure:

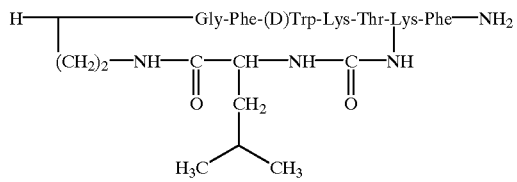

Figure 7:
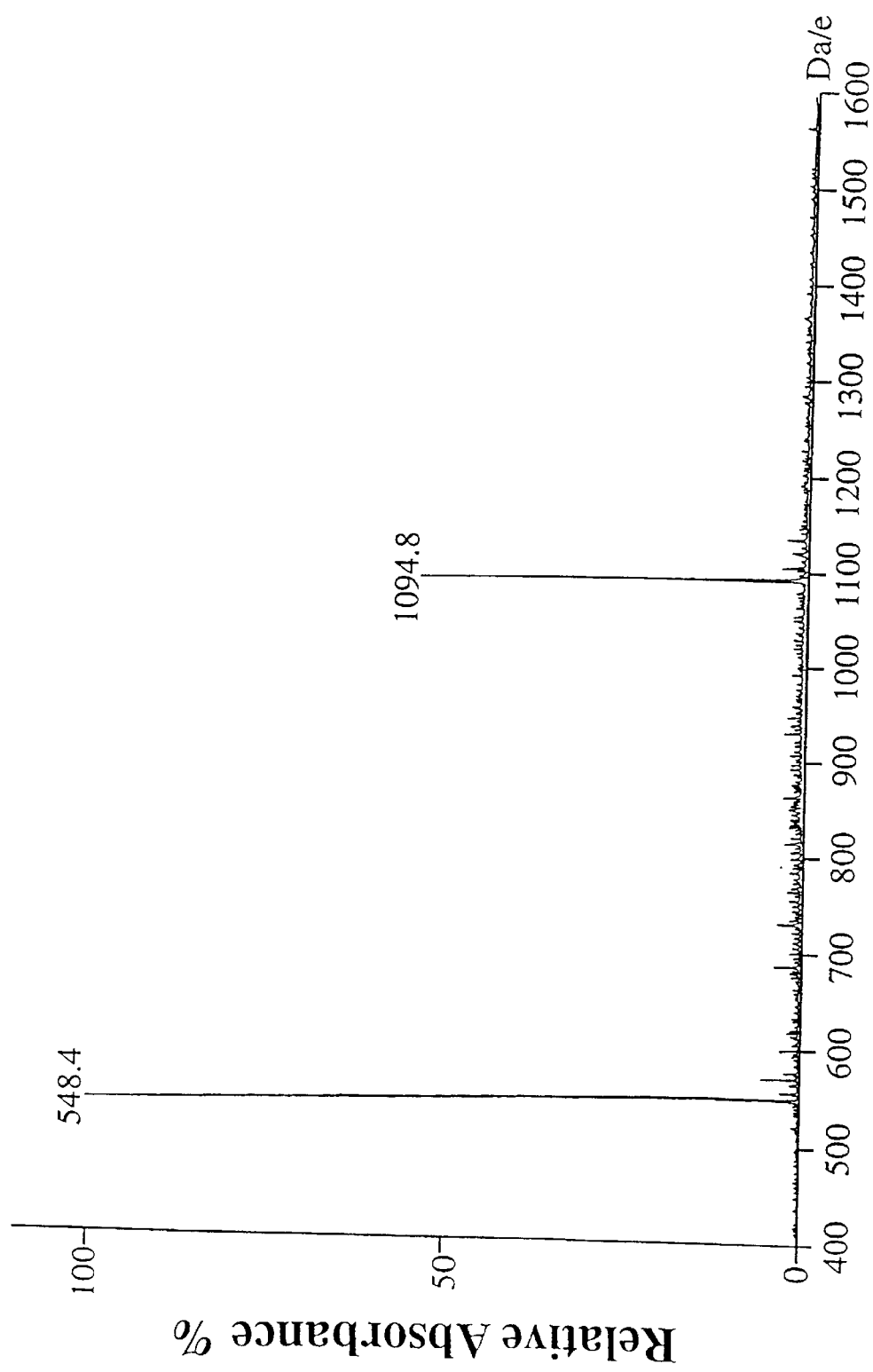
FIG. 7. Mass spectra analysis of PTR 3237 obtained in example 65 A.

The mass spectra analysis of the crude peptide are represented in FIG. 7.

B. Formation of urea bond in the sequence by using diamine as follows: To 5 eq of mono Fmoc-diamine hydrochlorid in CH$_2$Cl$_2$ (0.15 M), 1 eq DIEA (for neutralization of the hydrochloride) was added. After 1 min 1.65 eq of BTC were added and the suspension was stirred for 2 minutes, followed by addition of 14 eq of DIEA. After 1 minute, the resulted solution was added to the peptidyl resin and the mixture was agitated for 1 hour at room temperature followed by CH$_2$Cl$_2$ and NMP washes. The resulted backbone cyclic peptide analog denoted PTR 3241 has the following structure:

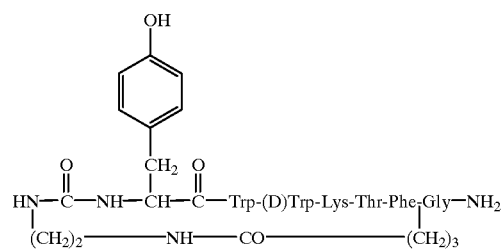

Figure 8:
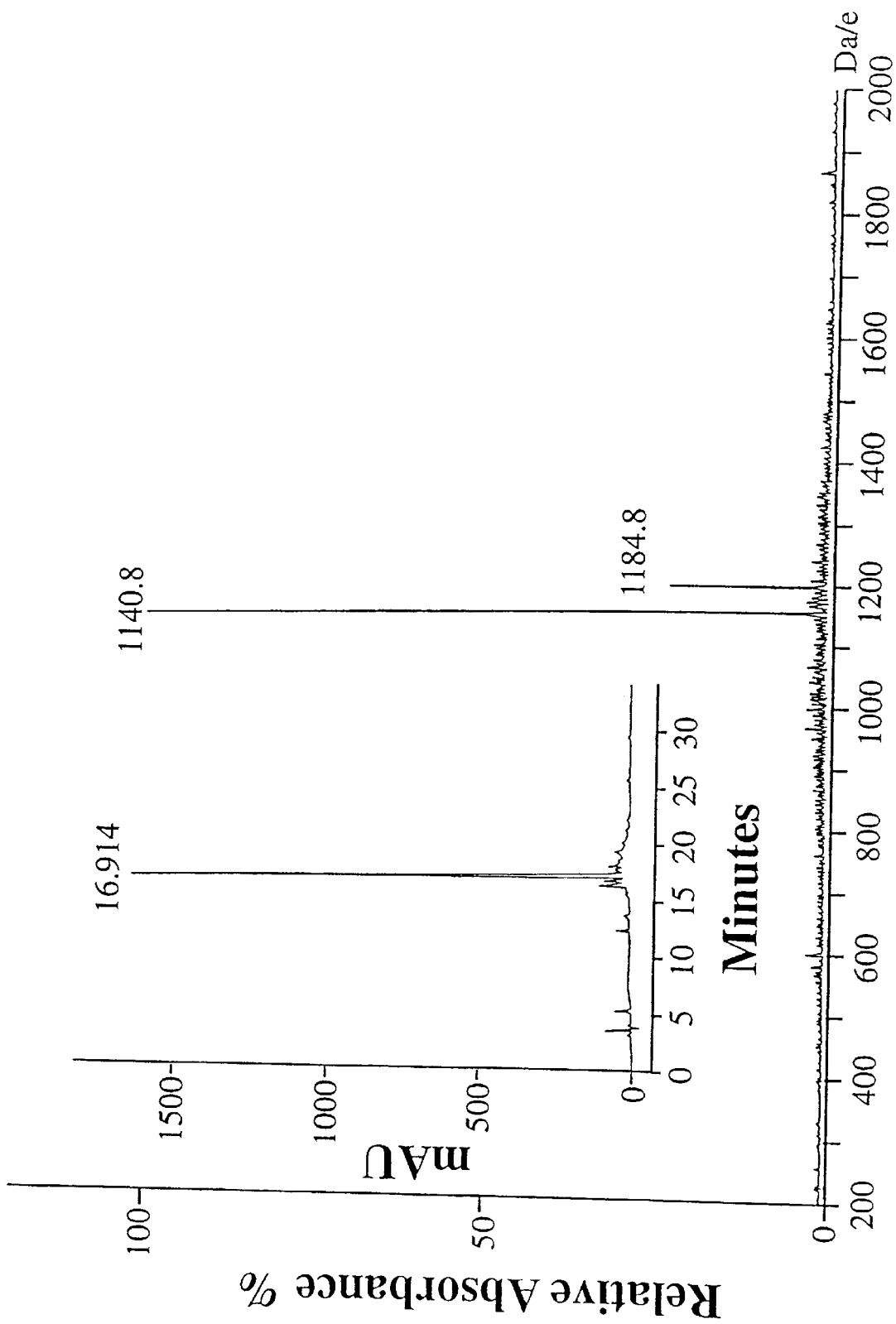
FIG. 8. HPLC chromatogram and mass spectra analysis of PTR 3241 obtained in example 65 B.

The HPLC chromatogram and the mass spectra analysis of the crude peptide are represented in FIG. 8.

Example 66

Multiple Parallel Synthesis using BTC

About 500 separate peptides were synthesized in MPS format using the BTC as coupling reagent. An example of synthesis results of 24 peptides is summarized in table 5.

TABLE 5

| | | | | | | | | | | | MS | |
|---|---|---|---|---|---|---|---|---|---|---|---|---|
| | | | | | | | | | | Calc. | qualitative results | Found |
| SEQ ID NO:5 | 1 | 1 | a | GlyN3 | Arg | Val | Gln | AlaC2 | Phe | Thr | 888.41 | (++) | 889.2 |
| SEQ ID NO:6 | 2 | 1 | b | GlyN3 | Arg | Pro | Gln | PheC2 | Phe | Thr | 962.42 | (++) | 963.1 |
| SEQ ID NO:7 | 3 | 1 | c | GlyN3 | Ala | Val | Gln | GlyC2 | Phe | Thr | 789.33 | (++) | 790.1 |
| SEQ ID NO:8 | 4 | 1 | d | GlyN3 | Tyr | Ala | Gln | LysC3 | Phe | Thr | 938.39 | (+−) | 938.9, 462.9 (cyclic tripep) |
| SEQ ID NO:9 | 5 | 1 | e | GlyN3 | Thr | Ser | Gln | LeuC3 | Phe | Thr | 877.36 | (++) | 878.1 |
| SEQ ID NO:10 | 6 | 1 | f | GlyN3 | Gly | Gly | Gln | ValC3 | Phe | Thr | 789.31 | (+−) | 790, 434 (cyclic tripep) |
| SEQ ID NO:11 | 7 | 1 | g | GlyN3 | Ala | Ala | Gly | AlaC2 | Phe | Thr | 704.28 | (++) | 705 |
| SEQ ID NO:12 | 8 | 1 | h | GlyN3 | Tyr | Gly | Gly | PheC2 | Phe | Thr | 858.31 | (++) | 859 |
| SEQ ID NO:13 | 9 | 2 | a | GlyN3 | Ile | Arg | Gly | GlyC2 | Phe | Thr | 817.36 | (++) | 818 |
| SEQ ID NO:14 | 10 | 2 | b | GlyN3 | Leu | Met | Gly | LysC3 | Phe | Thr | 877.37 | (++) | 878.1 |
| SEQ ID NO:15 | 11 | 2 | c | GlyN3 | Lys | Asp | Gly | LeuC3 | Phe | Thr | 861.36 | (++) | 862 |
| SEQ ID NO:16 | 12 | 2 | d | GlyN3 | Met | Ala | Gly | ValC3 | Phe | Thr | 806.31 | (++) | 806.9 |
| SEQ ID NO:17 | 13 | 2 | e | GlyN3 | Phe | Tyr | Ile | AlaC2 | Phe | Thr | 928.39 | (++) | 929 |
| SEQ ID NO:18 | 14 | 2 | f | GlyN3 | Pro | Ile | Ile | PheC2 | Phe | Thr | 904.42 | (+−) | 905, 553 (tripep + piper) |
| SEQ ID NO:19 | 15 | 2 | g | GlyN3 | Ser | Gly | Ile | GlyC2 | Phe | Thr | 748.29 | (++) | 748.9 |
| SEQ ID NO:20 | 16 | 2 | h | GlyN3 | Thr | Asp | Ile | LysC3 | Phe | Thr | 905.39 | (−) | 463 (tripep + piper) |
| SEQ ID NO:21 | 17 | 3 | a | GlyN3 | Trp | Asp | Ile | LeuC3 | Phe | Thr | 975.41 | (−) | 975.9, 448 (tripep + piper), 893.9 (?) |
| SEQ ID NO:22 | 18 | 3 | b | GlyN3 | Tyr | Gly | Ile | ValC3 | Phe | Thr | 880.37 | (−) | 881, 434 (tripep + piper), 865.9 (M—NH3) |
| SEQ ID NO:23 | 19 | 3 | c | GlyN3 | Val | Tyr | Leu | AlaC2 | Phe | Thr | 880.39 | (++) | 881 |
| SEQ ID NO:24 | 20 | 3 | d | GlyN3 | Phe | Asp | Leu | PheC2 | Phe | Thr | 956.39 | (++) | 956.9 |
| SEQ ID NO:25 | 21 | 3 | e | GlyN3 | Ile | Asp | Leu | GlyC2 | Phe | Thr | 832.35 | (++) | 832.9 |
| SEQ ID NO:26 | 22 | 3 | f | GlyN3 | Phe | Gln | Leu | LysC3 | Phe | Thr | 964.44 | (++) | 964.9 |

TABLE 5-continued

| | | | | | | | | | | | MS | |
| | | | | | | | | | | Calc. | qualitative results | Found |
|---|---|---|---|---|---|---|---|---|---|---|---|---|
| SEQ ID NO:27 | 23 | 3 | g | GlyN3 | Glu | Ser | Leu | LeuC3 | Phe | Thr | 890.37 | (++) | 891 |
| SEQ ID NO:28 | 24 | 3 | h | GlyN3 | Gln | Pro | Leu | ValC3 | Phe | Thr | 885.4 | (++) | 886 |

Notes to Table 5:
Difficult coupling procedure: pre-activation of the AA outside of an automatic peptide synthesizer (ACT 396 with Labtech 4 from Advanced ChemTech).
Five eq AA in 150 ul dioxane + 1.65 eq BTC in 150 ul dichloropropane, mixing, after 1 mm 14 eq collidine in dichloropropane were added.
The pre-activated amino acids were transferred to the plate manually.
Reaction for 3 times 1 h at 60° C.

Figure 9:
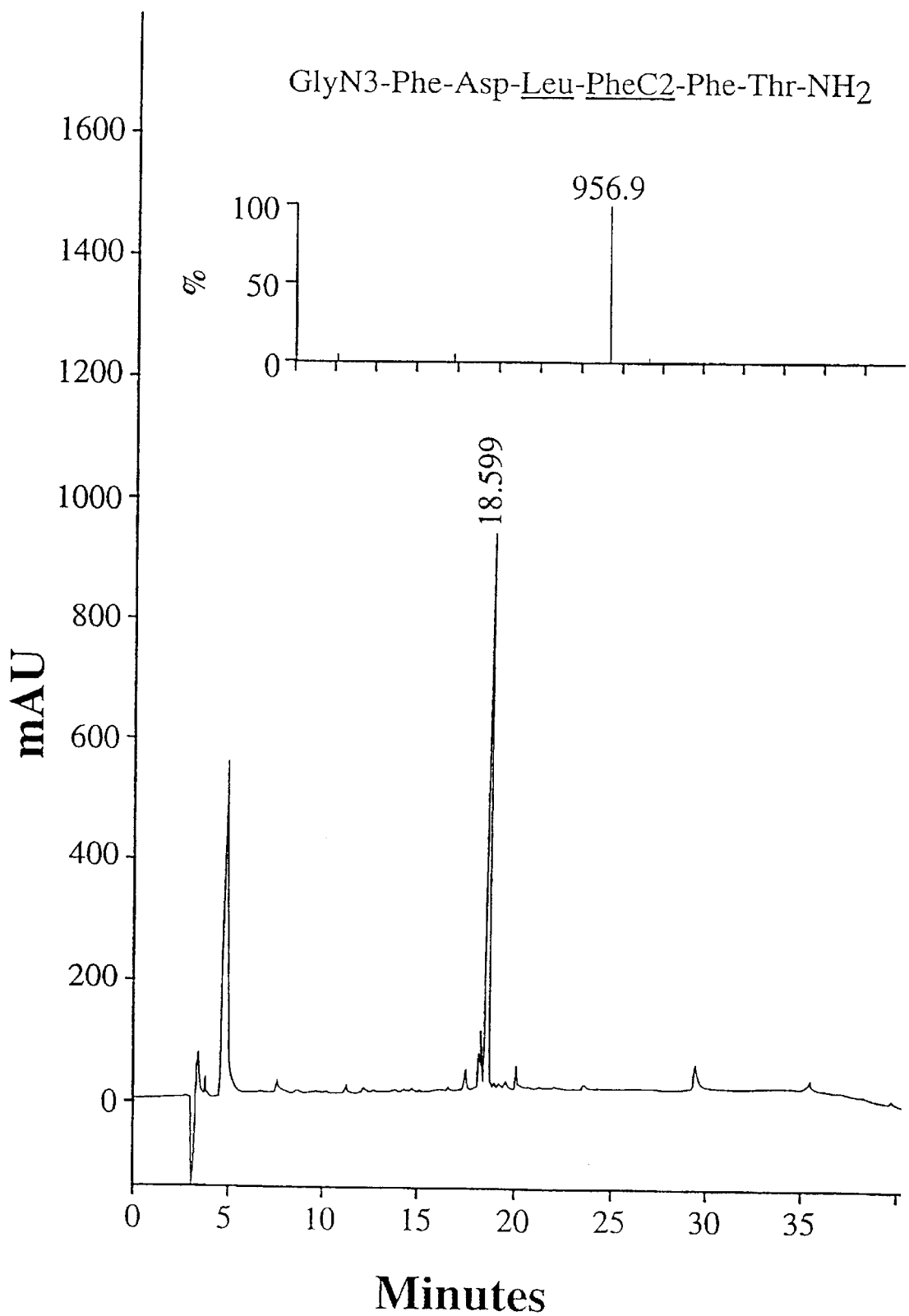
FIG. 9. HPLC chromatogram and mass spectra analysis of MPS peptide number 20, obtained in example 66.

HPLC chromatogram and mass spectra analysis examples of crude MPS peptide (number 20 in table 5), are represented in FIG. 9.

Example 67

Synthesis of a Cyclosporine analog using BTC

The BTC reagent was used for the difficult couplings in the synthesis of a Cyclosporine analog having the sequence:

Ala-NMeLeu-NMeLeu-NMeVal-NMeLeu-Abu-Sar-NMeLeu-Val-NMeLeu-Ala-NH$_2$

Figure 10:
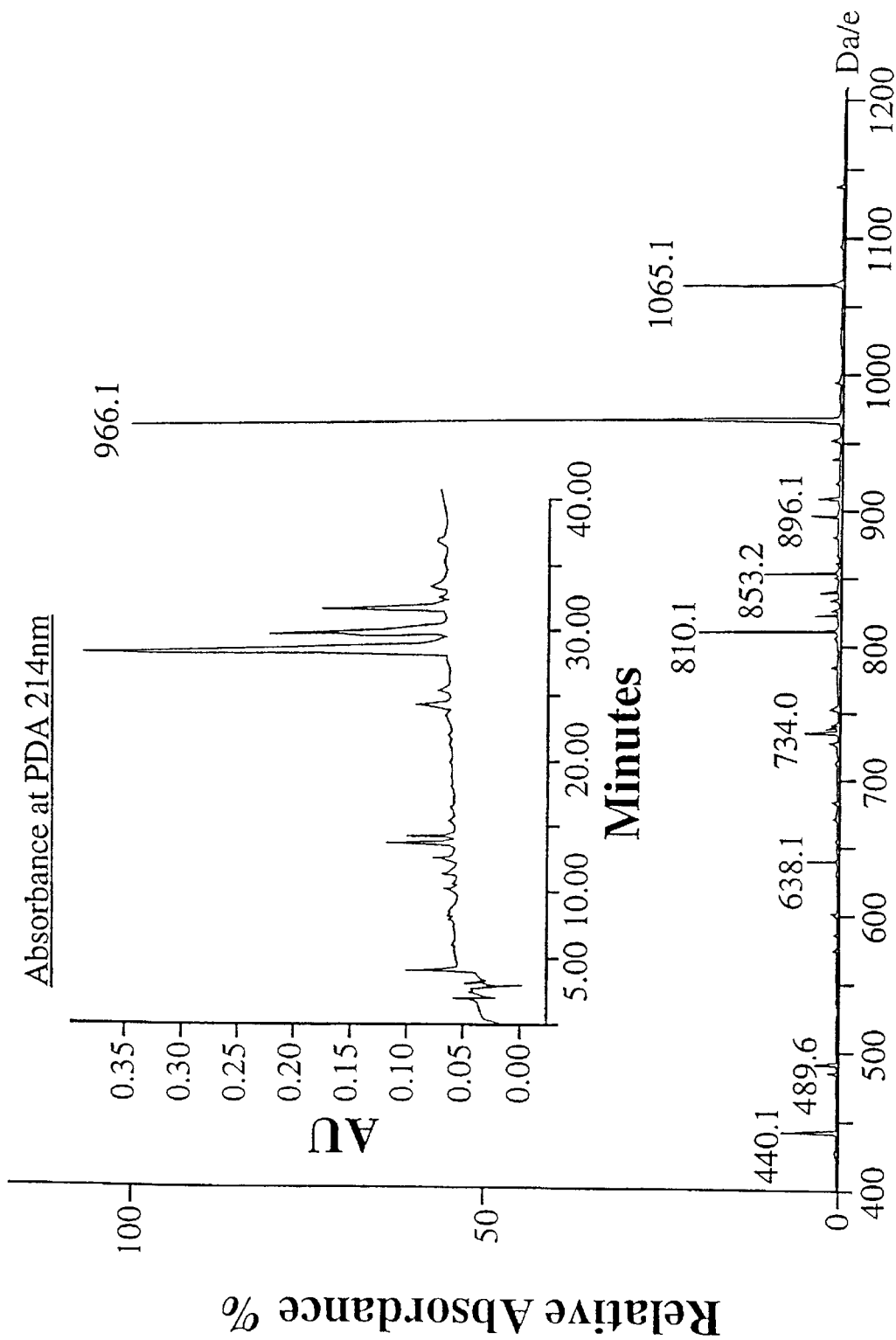
FIG. 10. HPLC chromatogram and mass spectra analysis of a Cyclosporine analog synthesized in example 67.

This peptidemimetic is a linear derivative of the Cyclosporin analog described in Raman et al. J. Org. Chem. 63:5734, 1998. The HPLC chromatogram and mass spectra analysis of the crude peptide are represented in FIG. 10.

What is claimed is:

1. A process of coupling an amino acid residue to a peptide chain which comprises:
   (i) providing an amino acid residue having a free carboxylic group and blocked amino group, optionally having additional blocked finctional side chains;
   (ii) reacting the blocked amino acid with bis-(trichloromethyl)carbonate in a solvent inert to this reaction to obtain an amino acid chloride;
   (iii) neutralizing the free acid with an organic base;
   (iv) adding the resulting suspension containing the amino acid chloride to a compound selected from the group consisting of a peptide having a blocked carboxyl terminus and a free amino terminus, and a peptidyl resin having at least one free amino terminus; and
   (v) providing reaction conditions enabling the coupling of the amino acid chloride to the peptide to yield a peptide elongated by one amino acid residue.

2. The process of claim 1 wherein the peptide chain comprises a sterically hindered residue in the N terminal position.

3. The process of claim 2 further comprising heating the reaction mixture during the coupling of the amino acid chloride to the peptide.

4. The process of claim 1 further comprising adding a catalyst to the reaction mixture of the amino acid chloride and the peptide.

5. The process of claim 2 wherein the sterically hindered residue in the N terminal position of the peptide chain comprises a sterically hindered secondary amine.

6. The process of claim 2 wherein the sterically hindered residue in the N terminal position of the peptide chain comprises an N-alpha (ω-functionalized) alkyl amino acid residue.

7. The process of claim 1 wherein the inert solvent is selected form the group consisting of dioxane, tetrahydrofuran, diglyme and 1,3 dichloropropane.

8. The process of claim 1 wherein the peptide coupling further comprises multiple parallel peptide synthesis.

9. The process of claim 1 wherein the coupling agent is provided at a stoichiometric ratio of at least about one third molar equivalent of the amino acid residue.

10. The process of claim 1 wherein the base is selected from the group consisting of collidine, diisopropylethylamine, pyridine, dimethyl pyridine and quinaldine.

11. The process of claim 1 wherein the amino group of the amino acid is blocked by a blocking group selected from the group consisting of fluorenylmethoxycarbonyl, and tert butoxycarbonyl.

12. A process of coupling an amino acid residue to a solid support which comprises:
   (i) providing an amino acid residue having a free carboxylic group and blocked amino group, optionally having additional blocked functional side chains;
   (ii) reacting the blocked amino acid with bis-(trichloromethyl)carbonate in a solvent inert to the reaction to obtain an amino acid chloride;
   (iii) neutralizing the free acid by addition of an organic base;
   (iv) adding the resulting suspension containing the amino acid chloride to a compound selected from the group consisting of a resin having at least one free amino terminus and a solid support having a functional group capable of binding the chloride; and
   (v) providing reaction conditions enabling the coupling of the amino acid chloride to the solid support.

13. In the in situ synthesis of peptides, the improvement which comprises synthesizing an amino acid chloride using one of bis-(trichloromethyl) carbonate, diphosgene or phosgene.

14. The invention of claim 13 wherein the peptides are synthesized during solid phase peptide synthesis.

* * * * *

UNITED STATES PATENT AND TRADEMARK OFFICE
CERTIFICATE OF CORRECTION

PATENT NO.     : 6,512,092 B2
DATED          : January 28, 2003
INVENTOR(S)    : Falb et al.

It is certified that error appears in the above-identified patent and that said Letters Patent is hereby corrected as shown below:

<u>Title page,</u>
Item [75], Inventors, change "Givaraim (IL)" to -- Givataim (IL) --.

<u>Column 39,</u>
Line 27, change "finctional" to -- functional --.
Line 58, change "selected form" to -- selected from --.

Signed and Sealed this

Third Day of June, 2003

JAMES E. ROGAN
*Director of the United States Patent and Trademark Office*

SEQUENCE LISTING

```
<160> NUMBER OF SEQ ID NOS: 28

<210> SEQ ID NO 1
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
<223> OTHER INFORMATION: Modified Trp residue with a carboxyl reactive
      group and a three carbon methylene spacer
<221> NAME/KEY: MOD_RES
<222> LOCATION: (6)..(6)
<223> OTHER INFORMATION: modified phenylalanine group with an amino
      reactive group and two carbon methylene spacers

<400> SEQUENCE: 1

Trp Ser Glu Tyr Leu Phe Gln
1               5

<210> SEQ ID NO 2
<211> LENGTH: 12
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (2)..(2)
<223> OTHER INFORMATION: modified alanine group with a carboxyl reactive
      group and a two carbon methylene spacer
<221> NAME/KEY: MOD_RES
<222> LOCATION: (11)..(11)
<223> OTHER INFORMATION: modified leucine group with an amino reactive
      group and three carbon methylene spacers

<400> SEQUENCE: 2

Thr Ala Ser Glu Asn His Leu Arg His Ala Leu Ser
1               5                   10

<210> SEQ ID NO 3
```

```
<211> LENGTH: 12
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (2)..(2)
<223> OTHER INFORMATION: modified alanine residue with a carboxyl
      reactive group and a three carbon methylene spacer
<221> NAME/KEY: MOD_RES
<222> LOCATION: (11)..(11)
<223> OTHER INFORMATION: modified leucine residue with an amino reactive
      group and a two carbon methylene spacer

<400> SEQUENCE: 3

Thr Ala Ser Glu Asn His Leu Arg His Ala Leu Ser
1               5                   10

<210> SEQ ID NO 4
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
<223> OTHER INFORMATION: Modified tryptophan residue with a carboxyl
      reactive group and a three carbon methylene spacer
<221> NAME/KEY: MOD_RES
<222> LOCATION: (5)..(5)
<223> OTHER INFORMATION: Modified leucine residue with an amino reactive
      group and a three carbon methylene spacer
<221> NAME/KEY: MOD_RES
<222> LOCATION: (5)..(6)
<223> OTHER INFORMATION: Between residues 5 and 6 is a
      3-aminomethylbenzoic acid residue

<400> SEQUENCE: 4

Trp Ser Glu Tyr Leu Ala Arg
1               5

<210> SEQ ID NO 5
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
<223> OTHER INFORMATION: modified Gly residue with an amino reactive
      group and three carbon methylene spacers
<221> NAME/KEY: MOD_RES
<222> LOCATION: (5)..(5)
<223> OTHER INFORMATION: modified Ala residue with a carboxyl reactive
      group and two carbon methylene spacers

<400> SEQUENCE: 5

Gly Arg Val Gln Ala Phe Thr
1               5

<210> SEQ ID NO 6
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
<223> OTHER INFORMATION: modified Gly residue with an amino reactive
```

```
        group and three carbon methylene spacers
<221> NAME/KEY: MOD_RES
<222> LOCATION: (5)..(5)
<223> OTHER INFORMATION: modified Phe residue with a carboxyl reactive
        group and two carbon methylene spacers

<400> SEQUENCE: 6

Gly Arg Pro Gln Phe Phe Thr
1               5

<210> SEQ ID NO 7
<211> LENGTH: 7
<212> TYPE: PRT
<213> ORGANISM: Artificial sequence
<220> FEATURE:
<223> OTHER INFORMATION: Hypothetical sequence for demonstration of the
        process
<221> NAME/KEY: MOD_RES
<222> LOCATION: (1)..(1)
<223> OTHER INFORMATION: modified Gly residue with an amino reactive
        group and three carbon methylene spacers
<221> NAME/KEY: MOD_RES
<222> LOCATION: (5)..(5)
<223> OTHER INFORMATION: modified Gly residue with a carboxyl reactive
        group and two carbon methylene spacers

<400> SEQUENCE: 7

Gly Ala Val Gln Gly Phe Thr
1               5

<210> SEQ ID NO 8
<211> LENGTH: 7
<212> TYPE: PRT
<213> ORGANISM: Artificial sequence
<220> FEATURE:
<223> OTHER INFORMATION: Hypothetical sequence for demonstration of the
        process
<221> NAME/KEY: MOD_RES
<222> LOCATION: (1)..(1)
<223> OTHER INFORMATION: modified Gly residue with an amino reactive
        group and three carbon methylene spacers
<221> NAME/KEY: MOD_RES
<222> LOCATION: (5)..(5)
<223> OTHER INFORMATION: modified Lys residue with a carboxyl reactive
        group and three carbon methylene spacers

<400> SEQUENCE: 8

Gly Tyr Ala Gln Lys Phe Thr
1               5

<210> SEQ ID NO 9
<211> LENGTH: 7
<212> TYPE: PRT
<213> ORGANISM: Artificial sequence
<220> FEATURE:
<223> OTHER INFORMATION: Hypothetical sequence for demonstration of the
        process
<221> NAME/KEY: MOD_RES
<222> LOCATION: (1)..(1)
<223> OTHER INFORMATION: modified Gly residue with an amino reactive
        group and three carbon methylene spacers
<221> NAME/KEY: MOD_RES
<222> LOCATION: (5)..(5)
<223> OTHER INFORMATION: modified leu residue with a carboxyl reactive
        group and three carbon methylene spacers

<400> SEQUENCE: 9

Gly Thr Ser Gln Leu Phe Thr
1               5

<210> SEQ ID NO 10
```

```
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
<223> OTHER INFORMATION: modified Gly residue with an amino reactive
      group and three carbon methylene spacers
<221> NAME/KEY: MOD_RES
<222> LOCATION: (5)..(5)
<223> OTHER INFORMATION: modified Val residue with a carboxyl reactive
      group and three carbon methylene spacers

<400> SEQUENCE: 10

Gly Gly Gly Gln Val Phe Thr
1               5

<210> SEQ ID NO 11
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
<223> OTHER INFORMATION: modified Gly residue with an amino reactive
      group and three carbon methylene spacers
<221> NAME/KEY: MOD_RES
<222> LOCATION: (5)..(5)
<223> OTHER INFORMATION: modified Ala residue with a carboxyl reactive
      group and two carbon methylene spacers

<400> SEQUENCE: 11

Gly Ala Ala Gly Ala Phe Thr
1               5

<210> SEQ ID NO 12
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
<223> OTHER INFORMATION: modified Gly residue with an amino reactive
      group and three carbon methylene spacers
<221> NAME/KEY: MOD_RES
<222> LOCATION: (5)..(5)
<223> OTHER INFORMATION: modified Phe residue with a carboxyl reactive
      group and two carbon methylene spacers

<400> SEQUENCE: 12

Gly Tyr Gly Gly Phe Phe Thr
1               5

<210> SEQ ID NO 13
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
<223> OTHER INFORMATION: modified Gly residue with an amino reactive
      group and three carbon methylene spacers
<221> NAME/KEY: MOD_RES
<222> LOCATION: (5)..(5)
<223> OTHER INFORMATION: modified Gly residue with a carboxyl reactive
```

```
      group and two carbon methylene spacers

<400> SEQUENCE: 13

Gly Ile Arg Gly Gly Phe Thr
1               5

<210> SEQ ID NO 14
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
<223> OTHER INFORMATION: modified Gly residue with an amino reactive
      group and three carbon methylene spacers
<221> NAME/KEY: MOD_RES
<222> LOCATION: (5)..(5)
<223> OTHER INFORMATION: modified Lys residue with a carboxyl reactive
      group and three carbon methylene spacers

<400> SEQUENCE: 14

Gly Leu Met Gly Lys Phe Thr
1               5

<210> SEQ ID NO 15
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (5)..(5)
<223> OTHER INFORMATION: modified Leu residue with a carboxyl reactive
      group and three carbon methylene spacers
<221> NAME/KEY: MOD_RES
<222> LOCATION: (1)..(1)
<223> OTHER INFORMATION: modified Gly residue with an amino reactive
      group and three carbon methylene spacers

<400> SEQUENCE: 15

Gly Lys Asp Gly Leu Phe Thr
1               5

<210> SEQ ID NO 16
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
<223> OTHER INFORMATION: modified Gly residue with an amino reactive
      group and three carbon methylene spacers
<221> NAME/KEY: MOD_RES
<222> LOCATION: (5)..(5)
<223> OTHER INFORMATION: modified Val residue with a carboxyl reactive
      group and three carbon methylene spacers

<400> SEQUENCE: 16

Gly Met Ala Gly Val Phe Thr
1               5

<210> SEQ ID NO 17
<211> LENGTH: 7
<212> TYPE: PRT
<213> ORGANISM: Artificial sequence
<220> FEATURE:
```

```
<223> OTHER INFORMATION: Hypothetical sequence for demonstration of the
      process
<221> NAME/KEY: MOD_RES
<222> LOCATION: (1)..(1)
<223> OTHER INFORMATION: modified Gly residue with an amino reactive
      group and three carbon methylene spacers
<221> NAME/KEY: MOD_RES
<222> LOCATION: (5)..(5)
<223> OTHER INFORMATION: modified Ala residue with a carboxyl reactive
      group and two carbon methylene spacers

<400> SEQUENCE: 17

Gly Phe Tyr Ile Ala Phe Thr
1               5

<210> SEQ ID NO 18
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
<223> OTHER INFORMATION: modified Gly residue with an amino reactive
      group and three carbon methylene spacers
<221> NAME/KEY: MOD_RES
<222> LOCATION: (5)..(5)
<223> OTHER INFORMATION: modified Phe residue with a carboxyl reactive
      group and two carbon methylene spacers

<400> SEQUENCE: 18

Gly Pro Ile Ile Phe Phe Thr
1               5

<210> SEQ ID NO 19
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
<223> OTHER INFORMATION: modified Gly residue with an amino reactive
      group and three carbon methylene spacers
<221> NAME/KEY: MOD_RES
<222> LOCATION: (5)..(5)
<223> OTHER INFORMATION: modified Gly residue with a carboxyl reactive
      group and two carbon methylene spacers

<400> SEQUENCE: 19

Gly Ser Gly Ile Gly Phe Thr
1               5

<210> SEQ ID NO 20
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
<223> OTHER INFORMATION: modified Gly residue with an amino reactive
      group and three carbon methylene spacers
<221> NAME/KEY: MOD_RES
<222> LOCATION: (5)..(5)
<223> OTHER INFORMATION: modified Lys residue with a carboxyl reactive
      group and three carbon methylene spacers

<400> SEQUENCE: 20
```

```
Gly Thr Asp Ile Lys Phe Thr
1               5

<210> SEQ ID NO 21
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
<223> OTHER INFORMATION: modified Gly residue with an amino reactive
      group and three carbon methylene spacers
<221> NAME/KEY: MOD_RES
<222> LOCATION: (5)..(5)
<223> OTHER INFORMATION: modified Leu residue with a carboxyl reactive
      group and three carbon methylene spacers

<400> SEQUENCE: 21

Gly Trp Asp Ile Leu Phe Thr
1               5

<210> SEQ ID NO 22
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
<223> OTHER INFORMATION: modified Gly residue with an amino reactive
      group and three carbon methylene spacers
<221> NAME/KEY: MOD_RES
<222> LOCATION: (5)..(5)
<223> OTHER INFORMATION: modified Val residue with a carboxyl reactive
      group and three carbon methylene spacers

<400> SEQUENCE: 22

Gly Tyr Gly Ile Val Phe Thr
1               5

<210> SEQ ID NO 23
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
<223> OTHER INFORMATION: modified Gly residue with an amino reactive
      group and three carbon methylene spacers
<221> NAME/KEY: MOD_RES
<222> LOCATION: (5)..(5)
<223> OTHER INFORMATION: modified Ala residue with a carboxyl reactive
      group and two carbon methylene spacers

<400> SEQUENCE: 23

Gly Val Tyr Leu Ala Phe Thr
1               5

<210> SEQ ID NO 24
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
```

```
<223> OTHER INFORMATION: modified Gly residue with an amino reactive
      group and three carbon methylene spacers
<221> NAME/KEY: MOD_RES
<222> LOCATION: (5)..(5)
<223> OTHER INFORMATION: modified Phe residue with a carboxyl reactive
      group and two carbon methylene spacers

<400> SEQUENCE: 24

Gly Phe Asp Leu Phe Phe Thr
1               5

<210> SEQ ID NO 25
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
<223> OTHER INFORMATION: modified Gly residue with an amino reactive
      group and three carbon methylene spacers
<221> NAME/KEY: MOD_RES
<222> LOCATION: (5)..(5)
<223> OTHER INFORMATION: modified Gly residue with a carboxyl reactive
      group and two carbon methylene spacers

<400> SEQUENCE: 25

Gly Ile Asp Leu Gly Phe Thr
1               5

<210> SEQ ID NO 26
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
<223> OTHER INFORMATION: modified Gly residue with an amino reactive
      group and three carbon methylene spacers
<221> NAME/KEY: MOD_RES
<222> LOCATION: (5)..(5)
<223> OTHER INFORMATION: modified Lys residue with a carboxyl reactive
      group and three carbon methylene spacers

<400> SEQUENCE: 26

Gly Phe Asn Leu Lys Phe Thr
1               5

<210> SEQ ID NO 27
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
<223> OTHER INFORMATION: modified Gly residue with an amino reactive
      group and three carbon methylene spacers
<221> NAME/KEY: MOD_RES
<222> LOCATION: (5)..(5)
<223> OTHER INFORMATION: modified Leu residue with a carboxyl reactive
      group and three carbon methylene spacers

<400> SEQUENCE: 27

Gly Asp Ser Leu Leu Phe Thr
1               5
```

```
<210> SEQ ID NO 28
<211> LENGTH: 7
<212> TYPE: PRT
<213> ORGANISM: Artificial sequence
<220> FEATURE:
<223> OTHER INFORMATION: Hypothetical sequence for demonstration of the
      process
<221> NAME/KEY: MOD_RES
<222> LOCATION: (1)..(1)
<223> OTHER INFORMATION: modified Gly residue with an amino reactive
      group and three carbon methylene spacers
<221> NAME/KEY: MOD_RES
<222> LOCATION: (5)..(5)
<223> OTHER INFORMATION: modified Val residue with a carboxyl reactive
      group and three carbon methylene spacers

<400> SEQUENCE: 28

Gly Gln Pro Leu Val Phe Thr
1               5
```